United States Patent
Chen et al.

(10) Patent No.: US 6,825,215 B2
(45) Date of Patent: Nov. 30, 2004

(54) 1,1-DISUBSTITUTED CYCLIC INHIBITORS OF MATRIX METALLOPROTEASES AND TNF-α

(75) Inventors: Xiao-Tao Chen, Newark, DE (US); Chu-Biao Xue, Hockessin, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 148 days.

(21) Appl. No.: 10/043,627

(22) Filed: Jan. 9, 2002

(65) Prior Publication Data

US 2002/0137734 A1 Sep. 26, 2002

Related U.S. Application Data

(60) Provisional application No. 60/260,952, filed on Jan. 11, 2001.

(51) Int. Cl.[7] ..................... A61D 31/47; C07D 401/12
(52) U.S. Cl. ..................... 514/314; 546/172; 546/174; 546/175
(58) Field of Search ............................ 514/314; 546/174

(56) References Cited

U.S. PATENT DOCUMENTS 5,179,105 A  1/1993  Igarashi et al.

FOREIGN PATENT DOCUMENTS

| EP | 780386 A | 6/1997 |
|---|---|---|
| EP | 818442 A | 1/1998 |
| WO | WO 9720824 A | 6/1997 |
| WO | WO 9732846 A | 9/1997 |
| WO | WO 9839316 A | 9/1998 |

OTHER PUBLICATIONS

Steward, Marimastat (BB2516): Current status of development, Cancer Chemother Pharmacol. 43(Suppl):S56–S60, 1999.*

* cited by examiner

*Primary Examiner*—Richard L. Raymond
*Assistant Examiner*—Liu Hong
(74) *Attorney, Agent, or Firm*—Jing S. Belfield; David H. Vance

(57) ABSTRACT

The present application describes novel 1,1-disubsituted cyclic derivatives of formula I:

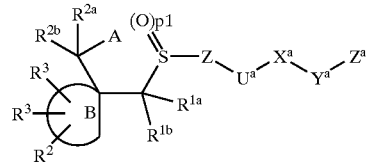

or pharmaceutically acceptable salt forms thereof, wherein ring B is a 3–8 membered non-aromatic ring consisting of: carbon atoms, 0–1 carbonyl groups, 0–1 double bonds, and from 0–2 ring heteroatoms selected from O, N, $NR^2$, S, S(O), and $S(O)_2$ and the other variables are defined in the present specification, which are useful as metalloprotease and as TNF-α inhibitors.

15 Claims, No Drawings

1,1-DISUBSTITUTED CYCLIC INHIBITORS OF MATRIX METALLOPROTEASES AND TNF-α

CROSS REFERENCE TO RELATED APPLICATIONS

This application claims the priority benefit of U.S. Provisional Application No. 60/260,952, filed Jan. 11, 2001, which is expressly incorporated fully herein by reference.

FIELD OF THE INVENTION

This invention relates generally to novel 1,1-disubstituted cyclic matrix metalloproteases and TNF-α inhibitors and pharmaceutical compositions containing the same and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase has been identified as providing the specific cleavage product of proteoglycan found in RA and OA patients (Lohmander L. S. et al. Arthritis Rheum. 36, 1993, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell-associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently it has been shown that a matrix metalloprotease or family of metalloproteases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also characterized by MMP-mediated tissue degradation, compounds which inhibit both MMPs and TNF production may also have a particular advantage in diseases where both mechanisms are involved.

EP 0,780,286 describes MMP inhibitors of formula A:

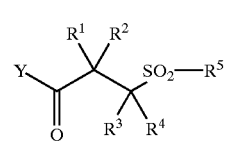

wherein Y can be NHOH, $R^1$ and $R^2$ can combine to form a cycloalkyl or heterocycloalkyl group, $R^3$ and $R^4$ can be a variety of groups including H, and $R^5$ can be substituted aryl. Such compounds are not considered to be part of the present invention.

WO 97/20824 depicts MMP inhibitors of formula B:

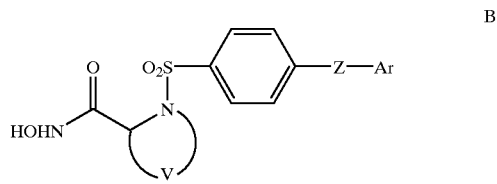

wherein ring V contains six atoms, Z is O or S, and Ar is an aryl or heteroaryl group. Ar is preferably a monocyclic aryl group with an optional para substituent or an unsubstituted monocyclic heteroaryl group. Compounds of this sort are not considered to be part of the present invention.

EP 0,818,442 illustrates MMP inhibitors of formula C:

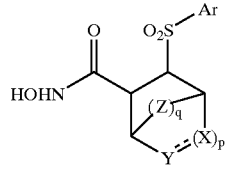

wherein Ar is optionally substituted phenyl or naphthyl, Z can be absent and X and Y can be a variety of substituents. Compounds like this are not considered to be part of the present invention.

WO 98/39316 presents MMP inhibitors of formula D:

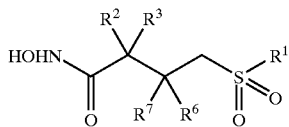

wherein $R^6$ and $R^7$ can combine to form a heterocycle and $R^1$ can be a substituted aryl group. These types of compounds are not considered to be part of the present invention.

WO 97/32846 describes MMP inhibitors of formula E:

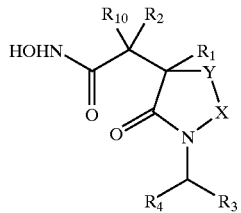

wherein $R_1$ can be a sulfonyl aryl group. Compounds of this sort are not considered to be part of the present invention.

The compounds of the present invention act as inhibitors of MPs, in particular aggrecanase and TNF-α. These novel molecules are provided as anti-inflammatory compounds and cartilage protecting therapeutics. The inhibition of aggrecanase, TNF-C, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, one object of the present invention is to provide novel cyclic hydroxamic acids useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders, comprising: administering to a host, in need of such treatment, a therapeutically effective amount of at least one of the compounds of the present invention or a pharmaceutically acceptable salt or prodrug form thereof.

These and other objects, which will become apparent during the following detailed description, have been achieved by the inventors'discovery that compounds of formula (I):

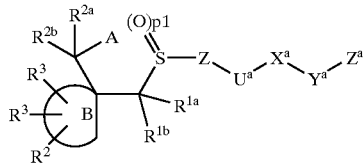

or pharmaceutically acceptable salt or prodrug forms thereof, wherein A, B, p1, $R^{1a}$, $R^{1b}$, $R^2$, $R^{2a}$, $R^{2b}$ $R^3$, $U^a$, $X^a$, $Y^a$, Z, and $Z^a$ are defined below, are effective metalloprotease inhibitors.

DETAILED DESCRIPTION OF PREFERRED EMBODIMENTS

[1] Thus, in an embodiment, the present invention provides a novel compound of formula I:

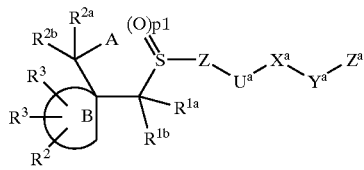

or a stereoisomer or pharmaceutically acceptable salt form thereof, wherein;

A is selected from —$COR^5$, —$CO_2H$, $CH_2CO_2H$, —$CO_2R^6$, —CONHOH, —$CONHOR^5$, —$CONHOR^6$, —N(OH)CHO, —N(OH)$COR^5$, —SH, —$CH_2SH$, —$SONHR^a$, —$SN_2H_2R^a$, —$PO(OH)_2$, and —$PO(OH)NHR^a$;

ring B is a 3–10 membered carbocyclic or heterocyclic ring consisting of: carbon atoms, 0–1 carbonyl groups, 0–1 double bonds, and from 0–2 ring heteroatoms selected from O, N, $NR^2$, and $S(O)_p$, provided that ring B contains other than a S—S, O—O, or S—O bond and provided that N-$R^2$ forms other than an N—O, N—N, or N—S bond;

Z is absent or selected from a $C_{3-13}$ carbocyclic residue substituted with 0–5 $R^b$ and a 5–14 membered heterocycle consisting of: carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, OC(O), C(O)$NR^{a1}$, $NR^{a1}C(O)$, OC(O)O, OC(O)$NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or selected from O, $NR^{a1}$, $S(O)_p$, and C(O);

$Z^a$ is selected from a $C_{3-13}$ carbocyclic residue substituted with 0–5 $R^c$ and a 5–14 membered heterocycle consisting of: carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^{1a}$ is selected from H, $C_{1-4}$ alkyl, phenyl, benzyl, $CH_2OR^3$, and $CH_2NR^aR^{a1}$;

$R^{1b}$ is selected from H, $C_{1-4}$ alkyl, phenyl, benzyl, $CH_2OR^3$, and $CH_2NR^aR^{a1}$;

alternatively, $R^{1a}$ and $R^{1b}$ combine to form a 3–6 membered ring consisting of: carbon atoms and 0–1 heteroatoms selected from O, S, S(O), S(O)$_2$, and NR$^a$;

provided that when $R^{1a}$ and $R^{1b}$ are hydrogen and ring B is a heterocycle, then $Z^a$ is the following:

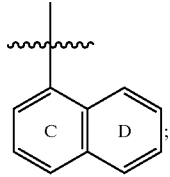

ring C is phenyl or pyridyl and is substituted with 0–2 R$^c$;
ring D is selected from phenyl, pyridyl, pyridazinyl, pyrimidyl, and pyrazinyl, and is substituted with 0–3 R$^c$;
$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_{r1}OC(O)(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q, $(CR^aR^{a1})_{r1}NR^aC(O)(CR^aR^{a1})_r$-Q, $(CR^aR^{a1})_{r1}OC(O)O(CR^aR^{a1})_r$-Q, $(CR^aR^{a1})_{r1}OC(O)NR^a(CR^aR^{a1})_r$-Q, $(CR^aR^{a1})_{r1}NR^aC(O)O(CR^aR^{a1})_r$-Q, $(CR^aR^{a1})_{r1}NR^aC(O)NR^a(CR^aR^{a1})_r$-Q, $(CR^aR^{a1})_{r1}S(O)_p(CR^aR^{a1})_r$-Q, $(CR^aR^{a1})_{r1}SO_2NR^a(CR^aR^{a1})_r$-Q $(CR^aR^{a1})_{r1}NR^aSO_2(CR^aR^{a1})_r$-Q, and $(CR^aR^{a1})_{r1}NR^aSO_2NR^a(CR^aR^{a1})_r$-Q;

$R^{2a}$ is selected from H, $C_{1-4}$ alkyl, phenyl, benzyl, $CH_2OR^3$, and $CH_2NR^aR^{a1}$;

$R^{2b}$ is selected from H, $C_{1-4}$ alkyl, phenyl, benzyl, $CH_2OR^3$, and $CH_2NR^aR^{a1}$;

alternatively, $R^{2a}$ and $R^{2b}$ combine to form a 3–6 membered ring consisting of: carbon atoms and 0–1 heteroatoms selected from O, S, S(O), S(O)$_2$, and NR$^a$;

Q is selected from H, a $C_{3-13}$ carbocyclic residue substituted with 0–5 $R^d$ and a 5–14 membered heterocycle consisting of: carbon atoms and 1–4 heteroatoms selected from the group consisting of N, O, and S(O)$_p$ and substituted with 0–5 $R^d$;

$R^3$, at each occurrence, is selected from $Q^1$, $C_{1-6}$ alkylene-$Q^1$, $C_{2-6}$ alkenylene-$Q^1$ $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1}_2)_{r1}S(O)_p(CR^aR^{a1})_r$-$Q^1$, and $(CR^aR^{a1})_{r1}SO_2NR^a(CR^aR^{a1})_r$-$Q^1$;

alternatively, when two $R^3$'s are attached to the same carbon atom, they combine to form a 3–8 membered carbocyclic or heterocyclic ring consisting of: carbon atoms and 0–3 heteroatoms selected from the group consisting of N, O, and S(O)$_p$ and substituted with 0–3 $R^d$;

$Q^1$ is selected from H, phenyl substituted with 0–3 $R^d$, naphthyl substituted with 0–3 $R^d$ and a 5–10 membered heteroaryl consisting of: carbon atoms and 1–4 heteroatoms selected from the group consisting of N, O, and S and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and S(O)$_p$;

$R^{a2}$, at each occurrence, is independently selected from $C_{1-4}$ alkyl, phenyl and benzyl;

$R^b$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, and CF$_2$CF$_3$;

$R^{b1}$, at each occurrence, is independently selected from OR$^a$, Cl, F, Br, I, =O, CN, NO$_2$, and NR$^a$R$^{a1}$;

$R^c$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, CF$_2$CF$_3$, $C_{3-10}$ carbocyclic residue and a 5–14 membered heterocycle consisting of: carbon atoms and 1–4 heteroatoms selected from the group consisting of N, O, and S(O)$_p$;

$R^d$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, CF$_2$CF$_3$, $C_{3-10}$ carbocyclic residue and a 5–14 membered heterocycle consisting of: carbon atoms and 1–4 heteroatoms selected from the group consisting of N, O, and S(O)$_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl] methyl, [5-(R$^a$)-1,3-dioxa-cyclopenten-2-one-yl]methyl, (5-aryl-1,3-dioxa-cyclopenten-2-one-yl)methyl, —$C_{1-10}$ alkyl-NR$^7$R$^{7a}$, —CH(R$^8$)OC(=O)R$^9$, and —CH(R$^8$)OC(=O)OR$^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

p1 is selected from 0, 1, and 2;

r, at each occurrence, is selected from 0, 1, 2, 3, and 4; and, r1, at each occurrence, is selected from 0, 1, 2, 3, and 4.

[2] In a preferred embodiment, the present invention provides a novel compound of formula II:

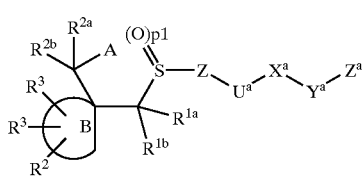

or a stereoisomer or pharmaceutically acceptable salt form thereof, wherein;

A is selected from —CO$_2$H, CH$_2$CO$_2$H, —CONHOH, —CONHOR$^5$, —CONHOR$^6$, —N(OH)CHO, —N(OH)COR$^5$, —SH, and —CH$_2$SH;

ring B is a 4–7 membered carbocyclic or heterocyclic ring consisting of: carbon atoms, 0–1 carbonyl groups, 0–1 double bonds, and from 0–2 ring heteroatoms selected from O, N, and NR$^2$, provided that ring B contains other than an O—O bond and provided that N—R$^2$ forms other than an N—O, N—N, or N—S bond;

Z is absent or selected from a C$_{3-6}$ carbocyclic residue substituted with 0–4 R$^b$ and a 5–6 membered heterocycle consisting of: carbon atoms and 1–4 heteroatoms selected from the group consisting of N, O, and S(O)$_p$ and substituted with 0–3 R$^b$;

U$^a$ is absent or is selected from: O, NR$^{a1}$, C(O), C(O)O, C(O)NR$^{a1}$, NR$^{a1}$C(O), S(O)$_p$, and S(O)$_p$NR$^{a1}$;

X$^a$ is absent or selected from C$_{1-4}$ alkylene and C$_{2-4}$ alkynylene;

Y$^a$ is absent or selected from O and NR$^{a1}$;

Z$^a$ is selected from H, a C$_{3-10}$ carbocyclic residue substituted with 0–5 R$^c$ and a 5–10 membered heterocycle consisting of: carbon atoms and 1–4 heteroatoms selected from the group consisting of N, O, and S(O)$_p$ and substituted with 0–5 R$^c$;

provided that Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

R$^2$ is selected from Q, C$_{1-6}$ alkylene-Q, C$_{2-6}$ alkenylene-Q, C$_{2-6}$ alkynylene-Q, (CR$^a$R$^{a1}$)$_{r1}$O(CR$^a$R$^{a1}$)$_r$-Q, (CR$^a$R$^{a1}$)$_{r1}$NR$^a$(CR$^a$R$^{a1}$)$_r$-Q, (CR$^a$R$^{a1}$)$_{r1}$C(O)(CR$^a$R$^{a1}$)$_r$-Q, (CR$^a$R$^{a1}$)$_{r1}$C(O)O(CR$^a$R$^{a1}$)$_r$-Q, (CR$^a$R$^{a1}$)$_r$C(O)NR$^a$R$^{a1}$, (CR$^a$R$^{a1}$)$_{r1}$C(O)NR$^a$(CR$^a$R$^{a1}$)$_r$-Q, (CR$^a$R$^{a1}$)$_{r1}$S(O)$_p$(CR$^a$R$^{a1}$)$_r$-Q, and (CR$^a$R$^{a1}$)$_{r1}$SO$_2$NR$^a$(CR$^a$R$^{a1}$)$_r$-Q;

Q is selected from H, a C$_{3-6}$ carbocyclic residue substituted with 0–5 R$^d$, and a 5–10 membered heterocycle consisting of: carbon atoms and 1–4 heteroatoms selected from the group consisting of N, O, and S(O)$_p$ and substituted with 0–5 R$^d$;

R$^a$, at each occurrence, is independently selected from H, C$_{1-4}$ alkyl, phenyl and benzyl;

R$^{a1}$, at each occurrence, is independently selected from H and C$_{1-4}$ alkyl;

alternatively, R$^a$ and R$^{a1}$ when attached to a nitrogen are taken together with the nitrogen to which they are attached to form a 5 or 6 membered ring comprising carbon atoms and from 0–1 additional heteroatoms selected from the group consisting of N, O, and S(O)$_p$;

R$^{a2}$, at each occurrence, is independently selected from C$_{1-4}$ alkyl, phenyl and benzyl;

R$^b$, at each occurrence, is independently selected from C$_{1-6}$ alkyl, OR$^a$, Cl, F, Br, =O, —CN, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, and CF$_3$;

R$^c$, at each occurrence, is independently selected from C$_{1-6}$ alkyl, OR$^a$, Cl, F, Br, =O, —CN, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, CF$_3$, C$_{3-6}$ carbocyclic residue and a 5–6 membered heterocycle consisting of: carbon atoms and 1–4 heteroatoms selected from the group consisting of N, O, and S(O)$_p$;

R$^d$, at each occurrence, is independently selected from C$_{1-6}$ alkyl, OR$^a$, Cl, F, Br, =O, —CN, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, CF$_3$, C$_{3-6}$ carbocyclic residue and a 5–6 membered heterocycle consisting of: carbon atoms and 1–4 heteroatoms selected from the group consisting of N, O, and S(O)$_p$;

R$^5$, at each occurrence, is selected from C$_{1-6}$ alkyl substituted with 0–2 R$^b$, and C$_{1-4}$ alkyl substituted with 0–2 R$^e$;

R$^e$, at each occurrence, is selected from phenyl substituted with 0–2 R$^b$ and biphenyl substituted with 0–2 R$^b$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, [5-(C$_1$-C$_5$ alkyl)-1,3-dioxa-cyclopenten-2-one-yl]methyl, [5-(Ra)-1,3-dioxa-cyclopenten-2-one-yl]methyl, (5-aryl-1,3-dioxa-cyclopenten-2-one-yl)methyl, —C$_{1-10}$ alkyl-NR$^7$R$^{7a}$, —CH(R$^8$)OC(=O)R$^9$, and —CH(R$^8$)OC(=O)OR$^9$;

R$^7$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^8$ is selected from H and C$_{1-4}$ linear alkyl;

R$^9$ is selected from H, C$_{1-6}$ alkyl substituted with 1–2 R$^f$, C$_{3-6}$ cycloalkyl substituted with 1–2 R$^f$, and phenyl substituted with 0–2 R$^b$;

R$^f$, at each occurrence, is selected from C$_{1-4}$ alkyl, C$_{3-6}$ cycloalkyl, C$_{1-5}$ alkoxy, and phenyl substituted with 0–2 R$^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

[3] In a more preferred embodiment, the present invention provides a novel compound of formula III:

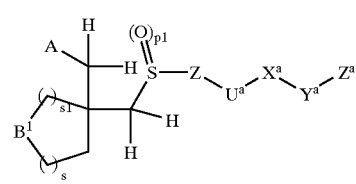

or a stereoisomer or pharmaceutically acceptable salt form thereof, wherein;

A is selected from —CO$_2$H, CH$_2$CO$_2$H, —CONHOH, —CONHOR$^5$, —N(OH)CHO, and —N(OH)COR$^5$;

B$^1$ is selected from NR$^2$, O, and CHR$^2$, provided that N—R$^2$ forms other than an N—O, N—N, or N—S bond;

Z is absent or selected from a C$_{5-6}$ carbocyclic residue substituted with 0–3 R$^b$ and a 5–6 membered heteroaryl comprising carbon atoms and from 1–4 heteroatoms selected from the group consisting of N, O, and S(O)$_p$ and substituted with 0–3 R$^b$;

U$^a$ is absent or is selected from: O, NR$^{a1}$, C(O), C(O)NR$^{a1}$, S(O)$_p$, and S(O)$_p$NR$^{a1}$;

$X^a$ is absent or selected from $C_{1-2}$ alkylene and $C_{2-4}$ alkynylene;

$Y^a$ is absent or selected from O and $NR^{a1}$;

$Z^a$ is selected from H, a $C_{5-6}$ carbocyclic residue substituted with 0–3 $R^c$ and a 5–10 membered heteroaryl comprising carbon atoms and from 1–4 heteroatoms selected from the group consisting of N, O, and $S(O)_p$ and substituted with 0–3 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a2})_{r1}C(O)NR^aR^{a1}$, $(CR^aR^{a2})_{r1}C(O)NR^a(CR^aR^{a1})_r$-Q, and $(CR^aR^{a1})_{r1}S(O)_p(CR^aR^{a1})_r$-Q;

Q is selected from H, a $C_{3-6}$ carbocyclic residue substituted with 0–3 $R^d$ and a 5–10 membered heterocycle consisting of: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a1}$ at each occurrence, is independently selected from H and $C_{1-4}$ alkyl;

$R_{a2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

r1, at each occurrence, is selected from 0, 1, 2, 3, and 4; and, s and s1 combine to total 1, 2, 3, or 4.

[4] In an even more preferred embodiment, the present invention provides a novel compound of formula IV:

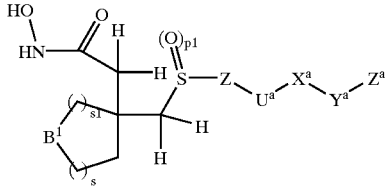

IV or a stereoisomer or pharmaceutically acceptable salt form thereof, wherein;

Z is absent or selected from phenyl substituted with 0–3 $R^b$ and pyridyl substituted with 0–3 $R^b$;

$U^a$ is absent or is O;

$X^a$ is absent or is selected from $CH_2$, $CH_2CH_2$, and $C_{2-4}$ alkynylene;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^2$ is selected from Q, $C_{1-6}$ alkylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

p, at each occurrence, is selected from 0, 1, and 2;

r, at each occurrence, is selected from 0, 1, 2, and 3;

r1, at each occurrence, is selected from 0, 1, 2, and 3; and, s and s1 combine to total 2, 3, or 4.

[5] In another preferred embodiment, the present invention provides a novel compound selected from the group:

N-hydroxy-2-{2-[({4-[(2-methyl-4-quinolinyl)methoxy]phenyl}sulfonyl)methyl]-2-pyrrolidinyl}acetamide;

N-hydroxy-2-{1-methyl-2-[({4-[(2-methyl-4-quinolinyl)methoxy]phenyl}sulfonyl)methyl]-2-pyrrolidinyl}acetamide;

N-hydroxy-2-{1-isobutyl-2-[({4-[(2-methyl-4-quinolinyl)methoxy]phenyl}sulfonyl)methyl]-2-pyrrolidinyl}acetamide;

N-hydroxy-2-{2-[({4-[(2-methyl-4-quinolinyl)methoxy]phenyl}sulfonyl)methyl]-1-(3-pyridinyl)-2-pyrrolidinyl}acetamide;

2-{1-acetyl-2-[({4-[(2-methyl-4-quinolinyl)methoxy]phenyl}sulfonyl)methyl]-2-pyrrolidinyl}-N-hydroxyacetamide;

N-hydroxy-2-{3-[({4-{(2-methyl-4-quinolinyl)methoxy]phenyl}sulfonyl)methyl]-3-pyrrolidinyl}acetamide;

N-hydroxy-2-{1-methyl-3-[({4-{(2-methyl-4-quinolinyl)methoxy]phenyl}sulfonyl)methyl]-3-pyrrolidinyl}acetamide;

N-hydroxy-2-{1-isopropyl-3-[({4-{(2-methyl-4-quinolinyl)methoxy]phenyl}sulfonyl)methyl]-3-pyrrolidinyl}acetamide;

N-hydroxy-2-{1-isobutyl-3-[({4-{(2-methyl-4-quinolinyl)methoxy]phenyl}sulfonyl)methyl]-3-pyrrolidinyl}acetamide;

N-hydroxy-2-{3-[({4-{(2-methyl-4-quinolinyl)methoxy]phenyl}sulfonyl)methyl]-1-neopentyl-3-pyrrolidinyl}acetamide;

N-hydroxy-2-{2-[({4-[(2-methyl-4-quinolinyl)methoxy]
   phenyl}sulfonyl)methyl]-2-piperidinyl}acetamide;
N-hydroxy-2-{1-methyl-2-[({4-[(2-methyl-4-quinolinyl)
   methoxy]phenyl}sulfonyl)methyl]-2-
   piperidinyl}acetamide;
N-hydroxy-2-{1-isobutyl-2-[({4-[(2-methyl-4-quinolinyl)
   methoxy]phenyl}sulfonyl)methyl]-2-
   piperidinyl}acetamide;
N-hydroxy-2-{3-[({4-[(2-methyl-4-quinolinyl)methoxy]
   phenyl}sulfinyl)methyl]-3-piperidinyl}acetamide;
N-hydroxy-2-{1-methyl-3-[({4-[(2-methyl-4-quinolinyl)
   methoxy]phenyl}sulfinyl)methyl]-3-
   piperidinyl}acetamide;
N-hydroxy-2-{1-isopropyl-3-[({4-[(2-methyl-4-quinolinyl)
   methoxy]phenyl}sulfinyl)methyl]-3-
   piperidinyl}acetamide;
N-hydroxy-2-{3-[({4-[(2-methyl-4-quinolinyl)methoxy]
   phenyl}sulfonyl)methyl]-3-piperidinyl}acetamide;
N-hydroxy-2-{1-methyl-3-[({4-[(2-methyl-4-quinolinyl)
   methoxy]phenyl}sulfonyl)methyl]-3-
   piperidinyl}acetamide;
N-hydroxy-2-{1-isopropyl-3-[({4-[(2-methyl-4-quinolinyl)
   methoxy]phenyl}sulfonyl)methyl]-3-
   piperidinyl}acetamide;
N-hydroxy-2-{1-isobutyl-3-[({4-[(2-methyl-4-quinolinyl)
   methoxylphenyl}sulfonyl)methyl]-3-
   piperidinyl}acetamide;
N-hydroxy-2-{4-[({4-[(2-methyl-4-quinolinyl)methoxy]
   phenyl}sulfonyl)methyl]-4-piperidinyl}acetamide;
N-hydroxy-2-{1-methyl-4-[({4-[(2-methyl-4-quinolinyl)
   methoxy]phenyl}sulfonyl)methyl]-4-
   piperidinyl}acetamide;
N-hydroxy-2-{2-[({4-[(2-methyl-4-quinolinyl)methoxy]
   phenyl}sulfonyl)methyl]tetrahydro-2-furanyl}acetamide;
N-hydroxy-2-{1-[({4-[(2-methyl-4-quinolinyl)methoxy]
   phenyl}sulfonyl)methyl]cyclobutyl}acetamide;
N-hydroxy-2-{1-[({4-[(2-methyl-4-quinolinyl)methoxy]
   phenyl}sulfinyl)methyl]cyclobutyl}acetamide;
N-hydroxy-2-{1-[({4-[(2-methyl-4-quinolinyl)methoxy]
   phenyl}sulfanyl)methyl]cyclobutyl}acetamide;
N-hydroxy-2-{1-[({4-[(2-methyl-4-quinolinyl) methoxy]
   phenyl}sulfonyl)methyl]cyclohexyl}acetamide;
N-hydroxy-2-{1-[({4-[(2-methyl-4-quinolinyl)methoxy]
   phenyl}sulfanyl)methyl]cyclohexyl}acetamide;
N-hydroxy-2-{3-[({4-[(2-methyl-4-quinolinyl)methoxy]
   phenyl}sulfonyl)methyl]-3-oxetanyl}acetamide;
N-hydroxy-2-{1-methyl-3-[({4-[(2-methyl-4-quinolinyl)
   methoxy]phenyl}sulfonyl)methyl]-2-
   oxopyrrolidinyl}acetamide;
N-hydroxy-2-{1-[({4-[(2-methyl-4-quinolinyl)methoxy]
   phenyl}sulfonyl)methyl]cyclopentyl}acetamide;
N-hydroxy-2-[5-[({4-[(2-methyl-4-quinolinyl)methoxy]
   phenyl}sulfonyl)methyl]-3-(3-pyridinyl)-4,5-dihydro-5-
   isoxazolyl]acetamide;
N-hydroxy-2-[5-[({4-[(2-methyl-4-quinolinyl)methoxy]
   phenyl}sulfonyl)methyl]-3-(4-pyridinyl)-4,5-dihydro-5-
   isoxazolyl]acetamide; and,
N-hydroxy-2-{4-[({4-[(2-methyl-4-quinolinyl)methoxy]
   phenyl}sulfonyl)methyl]tetrahydro-2H-pyran-4-
   yl}acetamide;

or a pharmaceutically acceptable salt form thereof.

In another embodiment, the present invention provides a novel pharmaceutical composition, comprising: a pharmaceutically acceptable carrier and a therapeutically effective amount of a compound of formula I or a pharmaceutically acceptable salt form thereof.

In another embodiment, the present invention provides a novel method for treating an inflammatory disorder, comprising: administering to a patient in need thereof a therapeutically effective amount of a compound of formula I or a pharmaceutically acceptable salt form thereof.

In another embodiment, the present invention provides a novel method, comprising: administering a compound of the present invention or a pharmaceutically acceptable salt form thereof in an amount effective to treat an inflammatory disorder.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula I or a pharmaceutically acceptable salt form thereof.

In another embodiment, the present invention provides a novel method of treating, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* [17]th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

A variety of compounds of formula (I) wherein A is a hydroxamic acid group can be produced in accordance with generic synthetic schemes 1–3. The hydroxyl group of key intermediate 1 is activated under the conditions known in literature (Scheme 1). One way to activate the hydroxyl group is to convert it to the corresponding halide. In scheme 1, only a few methods to make the corresponding bromide are listed for illustration purposes. But, this invention is not intended to be limited to these listed methods.

Another way to activate the hydroxyl group of compound 1 is to transform it to the corresponding sulfonate. The methanesulfonate, toluenesulfonate, and trifluoromethanesulfonate are included in scheme 1 for illustration purposes. Under suitable conditions, a mercaptan will displace the leaving group x of compound 2 to form product 3. The mercaptan used could be the whole right fragment necessary for formula (I) or just a portion of it. In the latter case, the whole right arm in formula (I) can be assembled later on via alkylation, Pd or Cu mediated coupling, acylation, etc. (see Scheme 4 for more details).

The oxidation of the sulphide can be achieved under a variety of conditions. Depending on what the goal is, either a sulphoxide or sulfone derivative can be made by controlling the stoichiometric ratio of the oxidation reagent to the substrate or by choosing different reagents. Basically, when the sulfone is required, Oxone® is the first choice if there are basic nitrogens or double bonds in the parent molecule. In order to oxidize sulphides to sulphoxides, sodium periodate is better than other reagents in term of chemoselectivity. There are a few reagents listed in scheme 1, such as MCPBA and TPAP/NaIO$_4$, which can be used to oxidize sulphides. But, this description is not intended to exclude any other reagents, which have a capacity to oxidize sulphides and are known in literature.

The hydroxamic acids can be prepared from their corresponding esters via several routes known in literature. The methyl or ethyl ester of compound 4 is directly converted to hydroxamic acid 5 by treatment with hydroxylamine under basic conditions such as KOH or NaOMe in solvents such as methanol. Alternatively, the t-butyl ester of compound 4 is converted to its carboxylic intermediate under TFA conditions. Coupling with hydroxylamine mediated by peptide coupling reagents such as BOP then affords the desired hydroxamic acid 5.

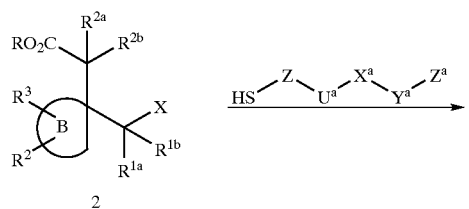

2

X = Cl, Br, I, OMs, OTs, OTf

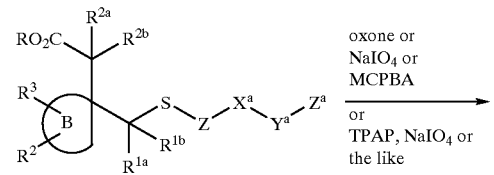

3

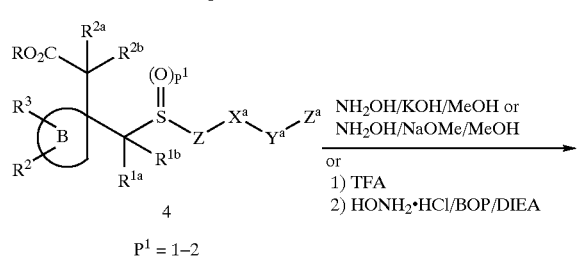

4

$P^1 = 1-2$

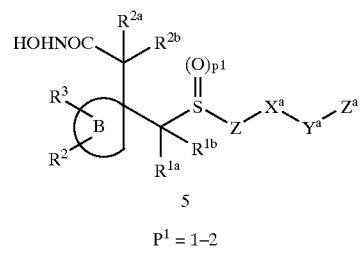

5

$P^1 = 1-2$

Intermediate 3 can also be made from the spirolactone 6 (Scheme 2). Under suitable conditions, opening the lactone by a mercaptan shown in scheme 2 results in the corresponding carboxylic acid 7. The mercaptan could be the whole fragment necessary for formula (I) or just a portion of it. In the latter case, the whole right arm can be assembled later on via alkylation, Pd or Cu mediated coupling, acylation, etc. (see Scheme 4 for more details). The carboxylic acid 7 is easily converted to the corresponding methyl ester 3 through the action of $CH_2N_2$, $TMSCHN_2$, or HCl/MeOH.

Scheme 1

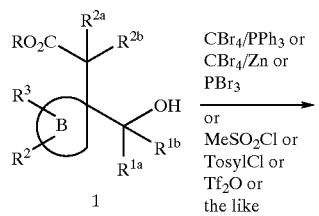

1

R = Me, Et, t-Bu

Scheme 2

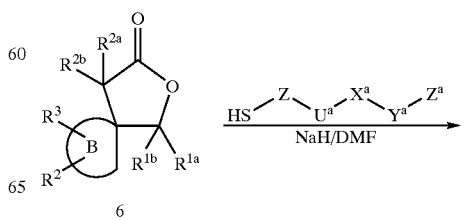

6

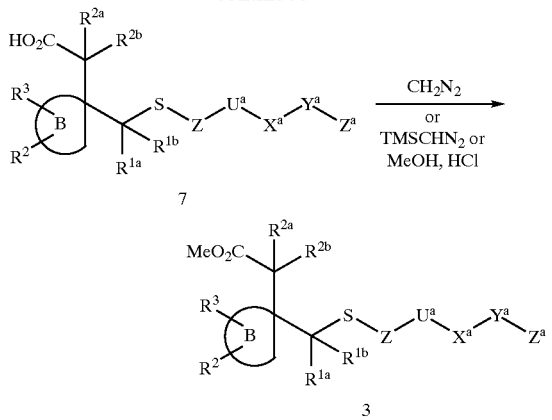

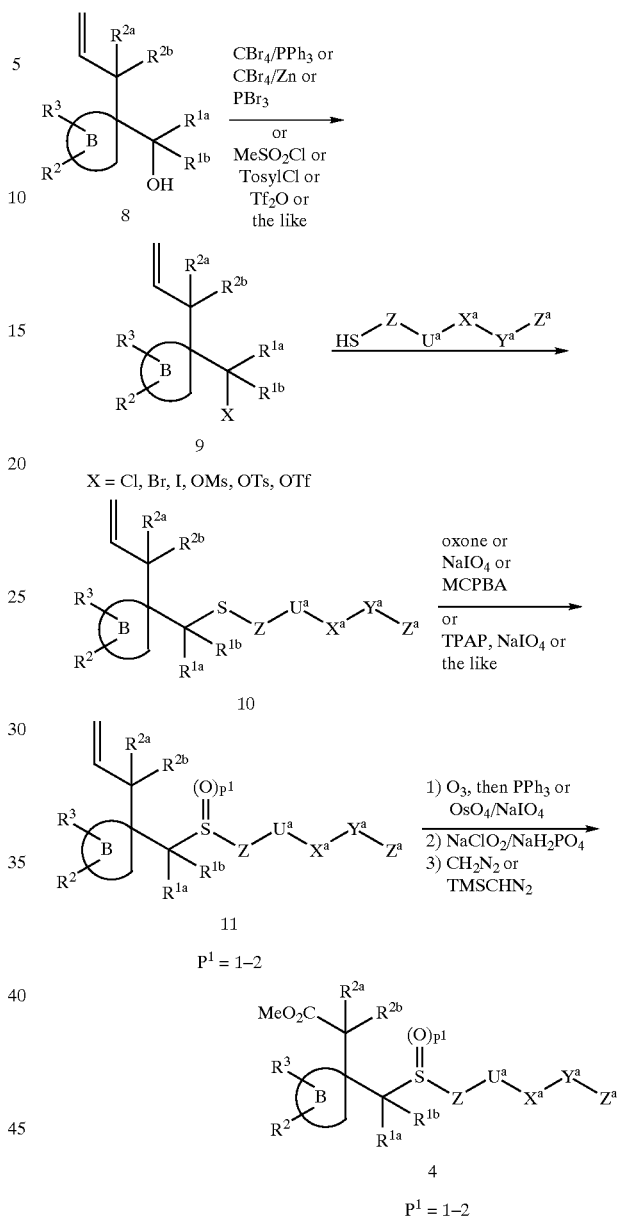

There is another attractive route to synthesize intermediate 4, starting from an alcohol 8 (scheme 3). The hydroxyl group of key intermediate 8 can be activated under the conditions known in literature. One way to activate the hydroxyl group is to convert it to the corresponding halide. In scheme 3, only a few methods to make the corresponding bromide are listed for illustration purposes. But, this invention is not intended to be limited to these listed methods. Another way to activate the hydroxyl group of compound 8 is to transform it to the corresponding sulfonate. The methanesulfonate, toluenesulfonate and trifluoromethanesulfonate are included in scheme 3 for illustration purpose.

Under suitable conditions, a mercaptan will displace leaving group x of compound 9 to form compound 10. The mercaptan could be the whole fragment necessary for formula (I) or just a portion of it. In the latter case, the whole right arm can be assembled later on via alkylation, Pd or Cu mediated coupling, acylation, etc. (see Scheme 4 for more details). The oxidation of the sulphide can be achieved under a variety of reaction conditions. Depending on what the goal is, either a sulphoxide or sulfone derivative can be made by controlling the stoichiometric ratio of the oxidation reagent with the substrate or by choosing different reagents. Basically, when the sulfone is required, Oxone® is the first choice if there are basic nitrogens or double bonds in the parent molecule. In order to oxidize sulphides to sulphoxides, sodium periodate is better than other reagents in term of chemoselectivity. There are a few reagents listed in scheme 3, such as MCPBA and TPAP/NaIO$_4$, which can be used to oxidize sulphides, but this invention does not exclude any other reagents, which have the capacity to oxidize sulphides and are known in literature.

In order to transform the allyl group of compound 11 to a two-carbon ester function, a three-step reaction sequence is executed. The first step is to cleave the carbon-carbon double bond to form the corresponding aldehyde. In scheme 3, two different methods are listed for illustration purposes. One method is ozonolysis. The other is dihydroxylation mediated by OsO$_4$, followed by cleavage of the corresponding vicinal diol mediated by NaIO$_4$. The next step is to oxidize the aldehyde to the corresponding carboxylic acid. It can be achieved under the conditions (NaClO$_2$/NaH$_2$PO$_4$/2-methyl-2-butene) as shown in scheme 3. But, this description is not intended to exclude any other known method, which fits this oxidation regimen.

The last step of the sequence is to convert the acid to the methyl ester 4. The simplest way to do it is shown in scheme 3. Both TMSCHN$_2$ and CH$_2$N$_2$ work well.

4-Mercaptophenol is one of the reagents that are used to prepare a variety of compounds of formula (I). When compound 2 (X=Cl, Br, I, OMs, OTs, or OTf) reacts with 4-mercaptophenol under basic conditions such as K$_2$CO$_3$ or NaH, in solvents such as acetone or DMF, a displacement takes place and the corresponding product 12 can be produced (Scheme 4). An alternative way to obtain compound 12 is through lactone intermediate 6. Upon heating the mixture of compound 6 and the anion of 4-mercaptophenol generated through the action of NaH in DMF, opening of the lactone of compound 6 affords the corresponding carboxylic acid, which is further transformed to methyl ester 12 through the action of TMSCHN$_2$. The only difference between compound 12 and 13 is the oxidation stage of sulfur atom.

Compound 13 can be made from intermediate 9. In this case, the allyl group of compound 9 has to be transformed to a two-carbon ester function after the introduction of 4-mercaptophenol. Once 4-mercaptophenol displaces the leaving group x in 9 under basic conditions, the resultant compound is subjected to ozonolysis and the cleavage of the terminal double bond affords the corresponding aldehyde. At the same time, the sulphide is oxidized to sulphoxide in situ. The sulphoxide can be reduced to sulphide or further be for this execution. Copper-mediated coupling of 12 (or 13) with aryl boric acid provides the biaryl ether (14b) and palladium-mediated coupling of the trifluoromethane-sulfonate derivative of compound 12 (or 13) with aryl boric acid affords the biaryl compound (14c).

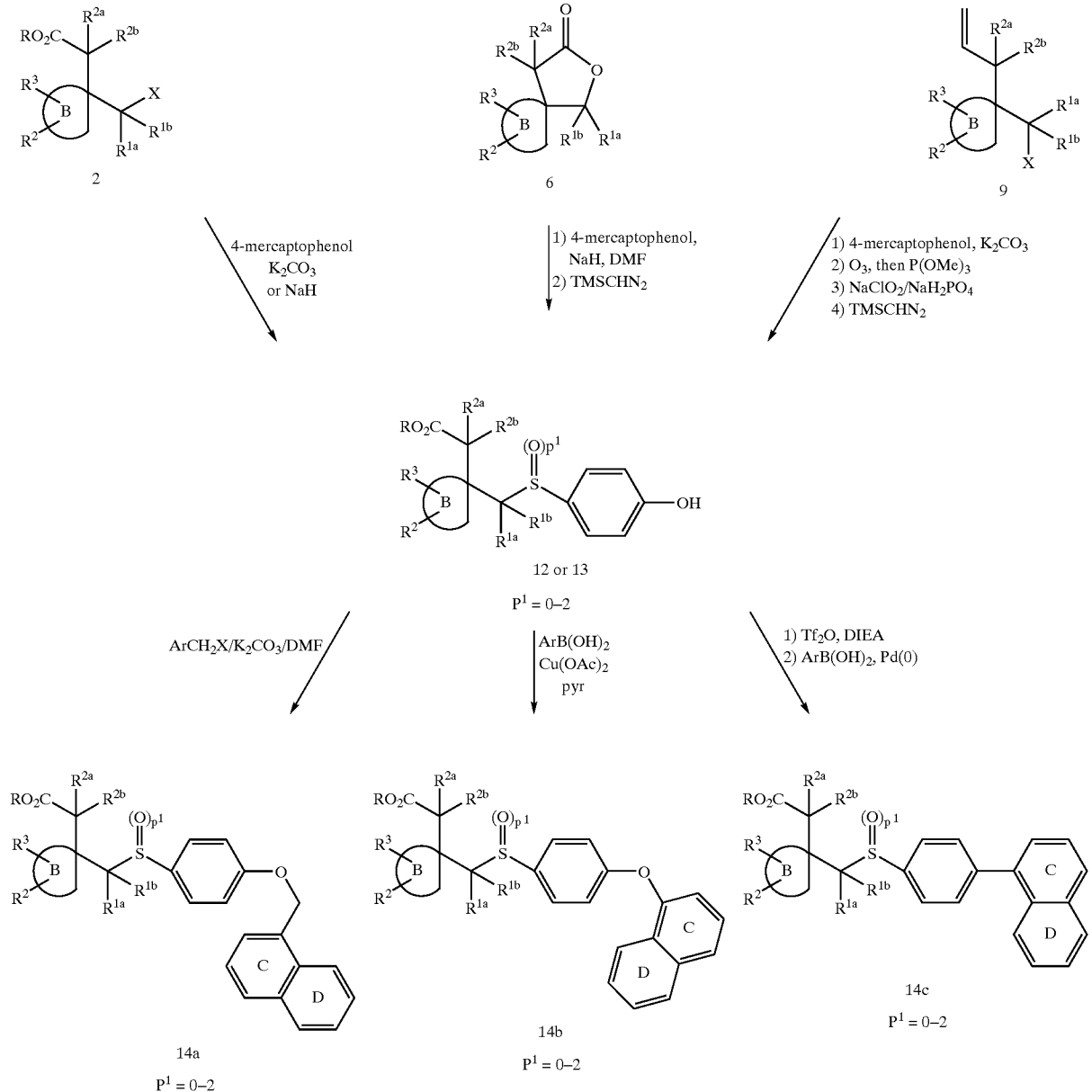

Scheme 4 oxidized to sulphone. After the aldehyde is oxidized by NaClO$_2$/NaH$_2$PO$_4$/2-methyl-2-butene, the resulting carboxylic acid is converted to methyl ester 13 using TMSCHN$_2$ as a methylation agent.

Intermediates 12 and 13 are converted to a variety of compounds such as 14a–c. If an alkylation is chosen to introduce the missing right arm to compounds 12 or 13, conditions like ArCH$_2$X/K$_2$CO$_3$/DMF are very convenient Conversion from compound 14 to hydroxamic acid 15 is rather straightforward (Scheme 5). Compound 14 is directly converted to hydroxamic acid 15 under conditions such as NH$_2$OH/KOH/MeOH if the sulfone function is already present in 14. Otherwise, a two-step sequence is required. This sequence includes an Oxone® oxidation and hydroxamic acid formation if the oxidation stage of sulfur in 14 has not reached the sulfone stage.

Scheme 5

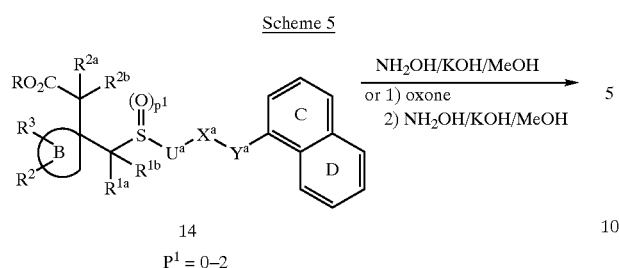

14
$P^1 = 0-2$

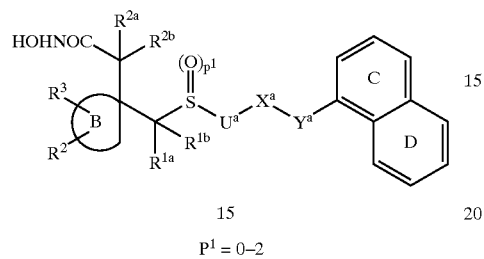

15
$P^1 = 0-2$

When a nitrogen is present in ring B of compound 14, a variety of compounds can be prepared by changing the substitution group on that nitrogen. The general strategy of this approach is outlined in scheme 6. After the parent compound 16 is assembled, the Boc protection group in 16 is removed under TFA conditions. A number of reactions can be utilized for preparation of different classes of compounds 18. For example, direct alkylation or reductive amination of compound 17 will introduce an alkyl side chain on the nitrogen (see compound 18). On the other hand, acylation of 17 will provide amide derivatives (see compound 18) and sulfonylation will lead to sulfonamide derivatives (see compound 18).

Scheme 6

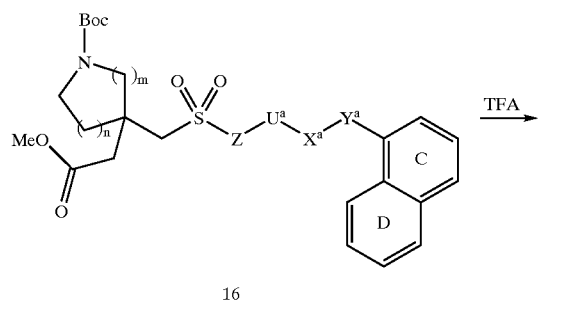

16
$m = 0-2$
$n = 0-3$ alkylation
reductive alkylation
acylation
sulfonylation

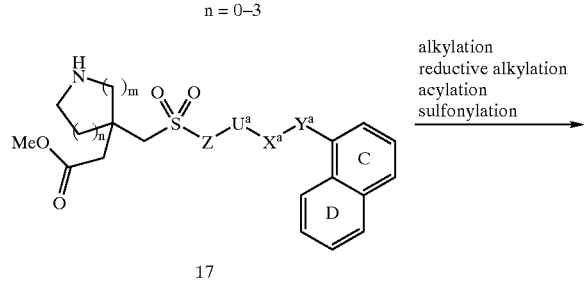

17

-continued

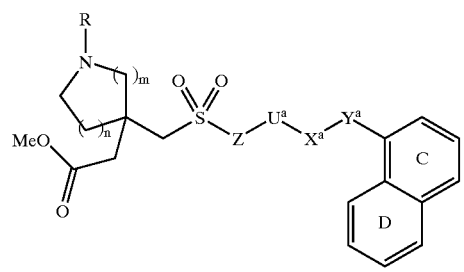

18

More complex scaffolds, other than nitrogen containing heterocycle, can be constructed and may provide favorable biological profiles. A few examples are outlined in scheme 7. If the central ring of compound 19 bears a functional group such as hydroxyl group, protected hydroxyl group, ketone, or ketal moiety at the designated position (see compound 19), this functional group provides a handle for further chemical elaboration. For example, when W in 19 is OH, the hydroxyl group can be oxidized to ketone derivative 20 (V=O) and the ketone may lead to alkene 20 (V=CH$_2$, CHR, or CR$_2$). If a cycloaddition reaction such as [3+2] is applied to the alkene substrate 20, a spiro product 22 can be obtained. Ring H in 22 can be a 3–7 membered carbocycle or heterocycle. When ring H is a heterocycle, the number of heteroatoms ranges from 1 to 3 and the heteroatoms include O, N and S.

Another way to form a spiro product from ketone 20 involves a Barbier-type addition to the ketone function, followed by ring formation. Similarly, compound 19 can be processed to an internal carbon-carbon double bond derivative 21. A number of reactions can be applied to substrate 21 and a bicyclic skeleton 23 can be built up based on cycloaddition approaches. The scope of ring H in 23 remains the same as that in 22.

Another derivation from compound 24 is to utilize enolate chemistry that allows a number of different electrophiles to be introduced next to either the ester function or the sulfone function (Scheme 8). Depending on where the electrophile is going to be introduced, different approaches can be pursued to achieve the desired product. For example, when an electrophile is going to be introduced next to the carbonyl group, the α-H of the sulfonyl function may compete with the α-H of the ester in the formation of the enolate (see compound 24). Fortunately, this complication can be easily avoided if a sulphide function is chosen instead of a sulfone function ($p^1=0$ in compound 24). On the other hand, when an electrophile is going to be introduced next to the sulfonyl group in 24, a carboxylic acid should not interfere in the introduction of the electrophile at the α-position of the sulfone. For further chemical elaboration of compound 25, a strategy outlined in Scheme 7 can be pursued as well.

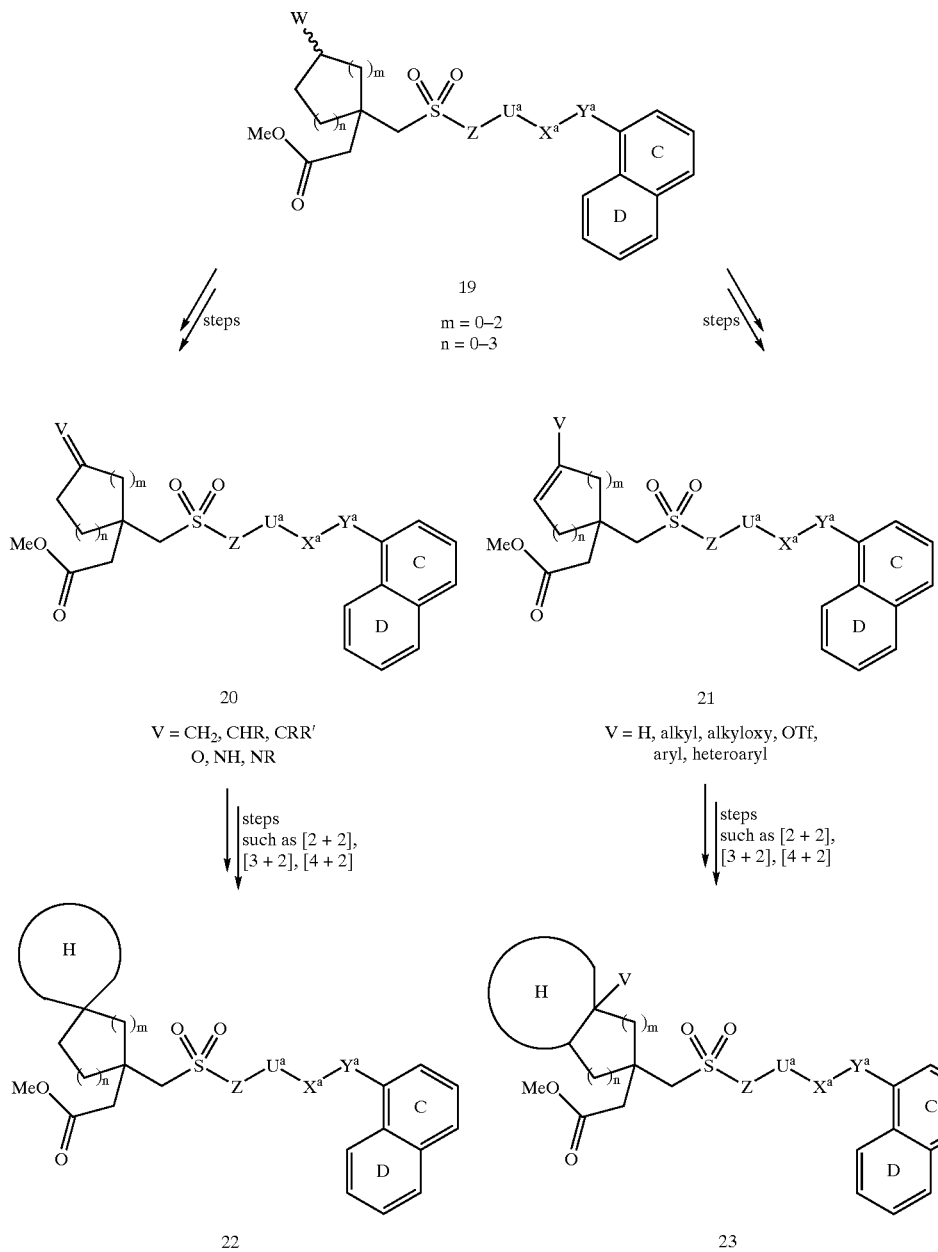
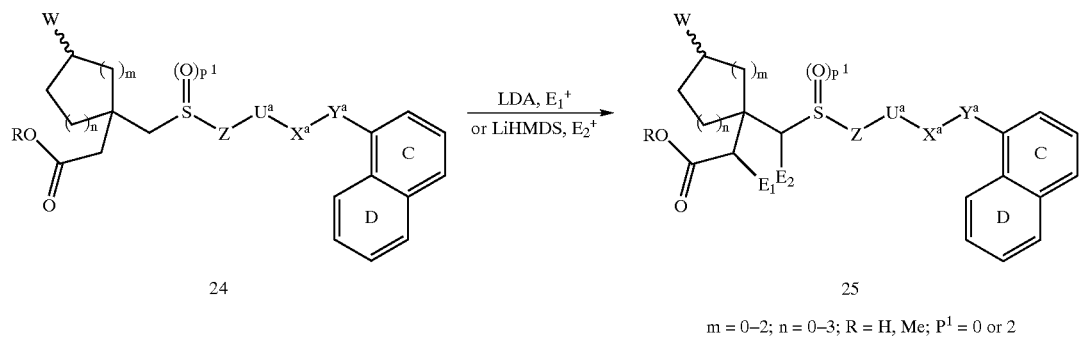

The synthesis of compound 35 is outlined in scheme 9. The orthoester Claisen rearrangement is the key step to establish a required quaternary carbon center (see compound 30). Cleavage of the carbon-carbon double bond in 30 by ozone, followed by reduction, leads to the intermediate 31. The rest of synthesis is straightforward and compound 35 is obtained in four steps.

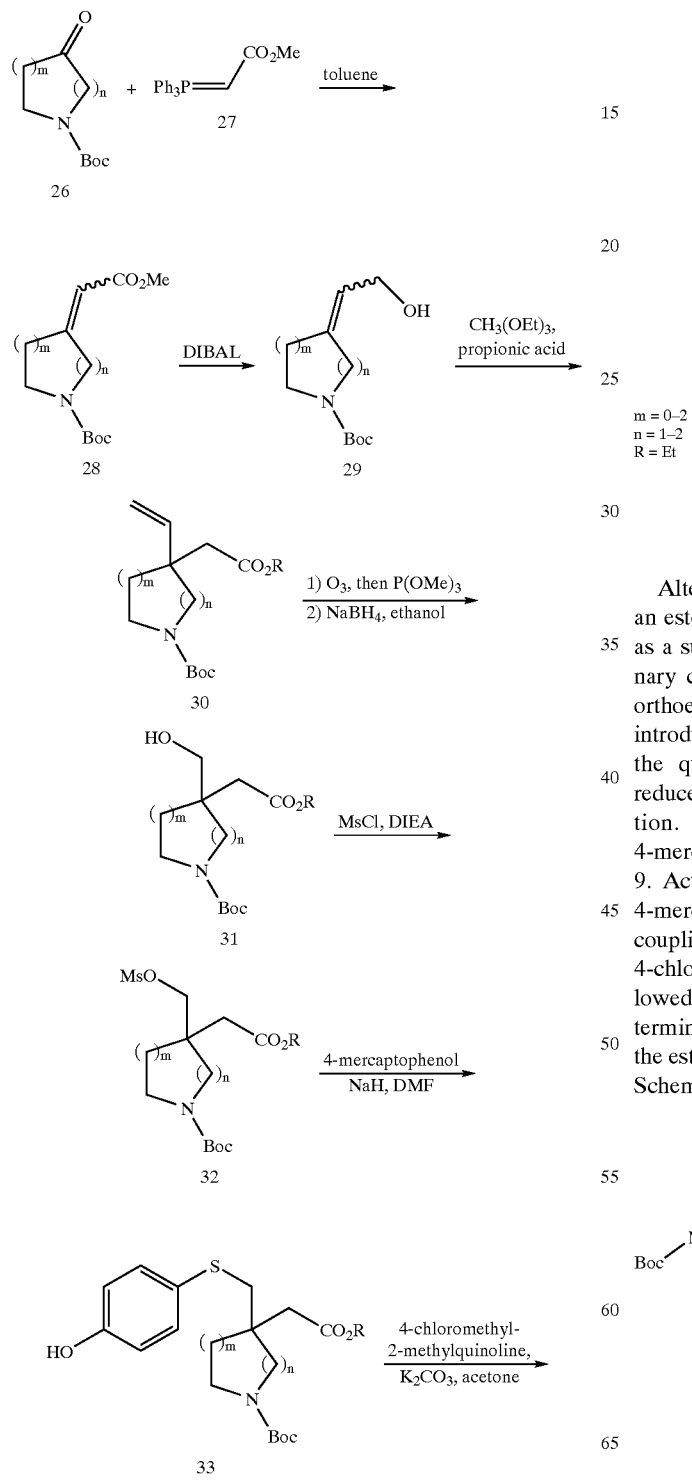

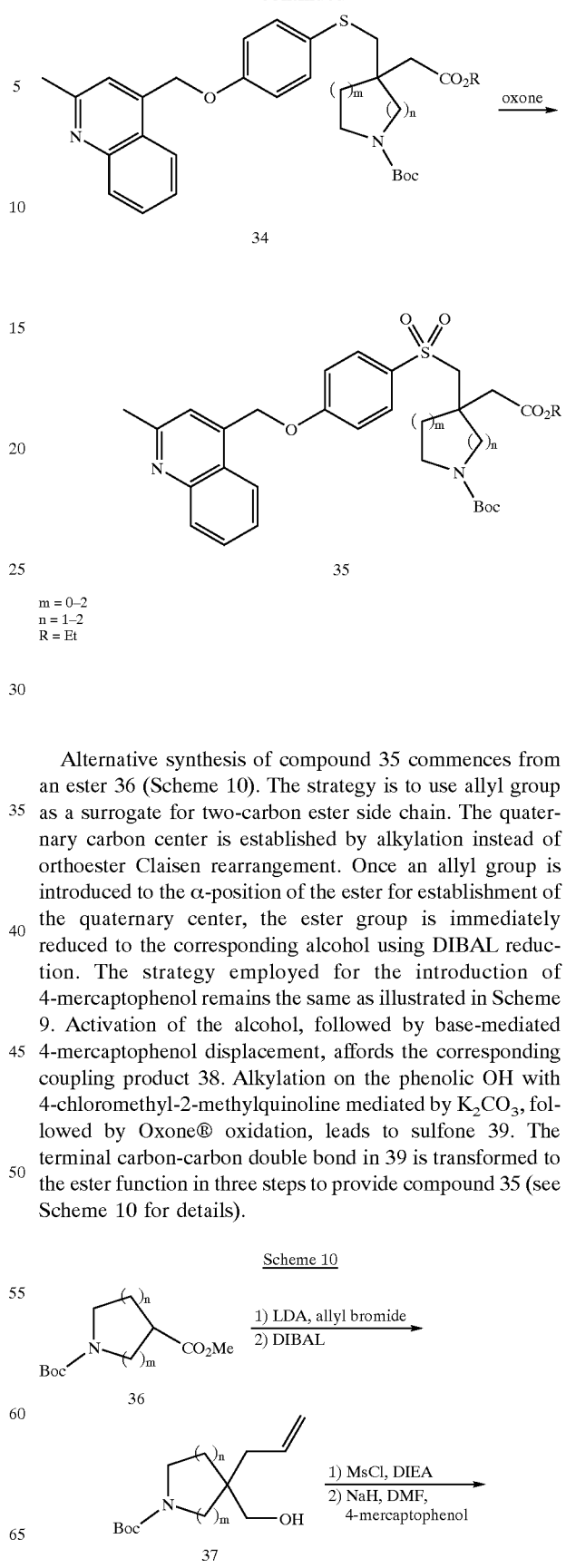

m = 0–2
n = 1–2
R = Et

Alternative synthesis of compound 35 commences from an ester 36 (Scheme 10). The strategy is to use allyl group as a surrogate for two-carbon ester side chain. The quaternary carbon center is established by alkylation instead of orthoester Claisen rearrangement. Once an allyl group is introduced to the α-position of the ester for establishment of the quaternary center, the ester group is immediately reduced to the corresponding alcohol using DIBAL reduction. The strategy employed for the introduction of 4-mercaptophenol remains the same as illustrated in Scheme 9. Activation of the alcohol, followed by base-mediated 4-mercaptophenol displacement, affords the corresponding coupling product 38. Alkylation on the phenolic OH with 4-chloromethyl-2-methylquinoline mediated by $K_2CO_3$, followed by Oxone® oxidation, leads to sulfone 39. The terminal carbon-carbon double bond in 39 is transformed to the ester function in three steps to provide compound 35 (see Scheme 10 for details).

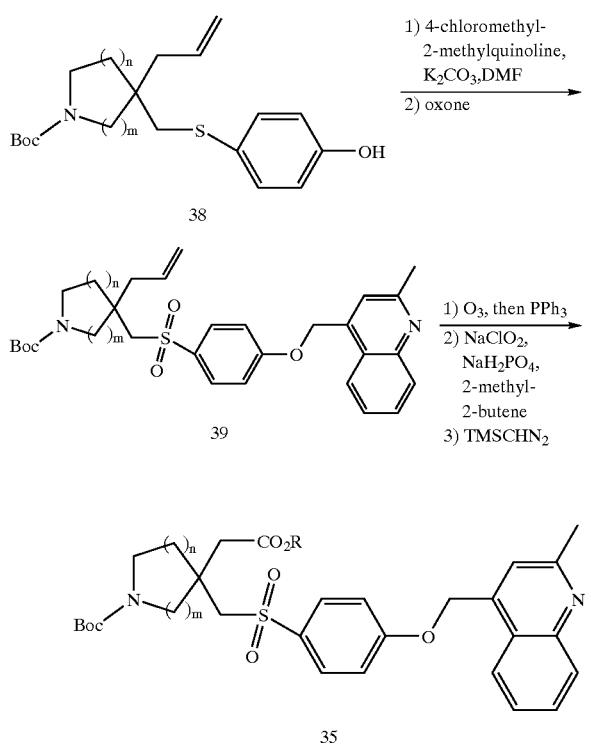

m = 0–3
n = 0–2
R = Me

An illustration for preparation of an oxygen-containing heterocycle 44a is provided in Scheme 11a. The chemistry employed remains exactly the same as seen in Scheme 10, but the starting material chosen this time is either a tetrahydrofuran derivative or a tetrahydropyran derivative 40a.

Scheme 11a

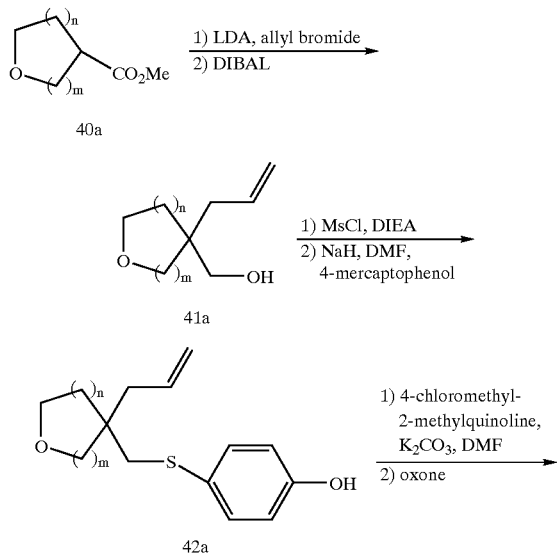

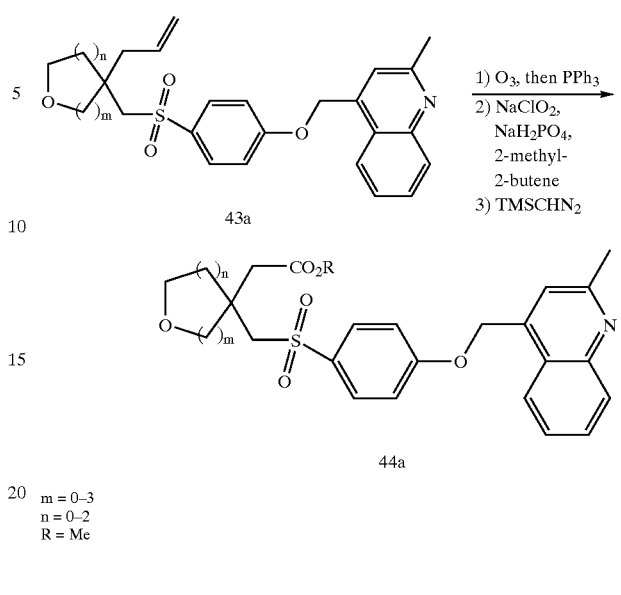

m = 0–3
n = 0–2
R = Me

An illustration for preparation of a carbocycle 44b is provided in Scheme 11b. The allylated compound 41b, obtained from allylation of starting material 40b, followed by DIBAL reduction, is subjected to ozonolysis and the resulting hemiacetal is further oxidized to lactone 42b immediately. Upon heating with NaH, 4-mercaptophenol in DMF, followed by treatment of TMSCHN$_2$ in methanol, lactone 42b is converted to compound 43b. After the quinoline moiety is introduced, Oxone® oxidation of the resulting material affords the final product 44b.

Scheme 11b

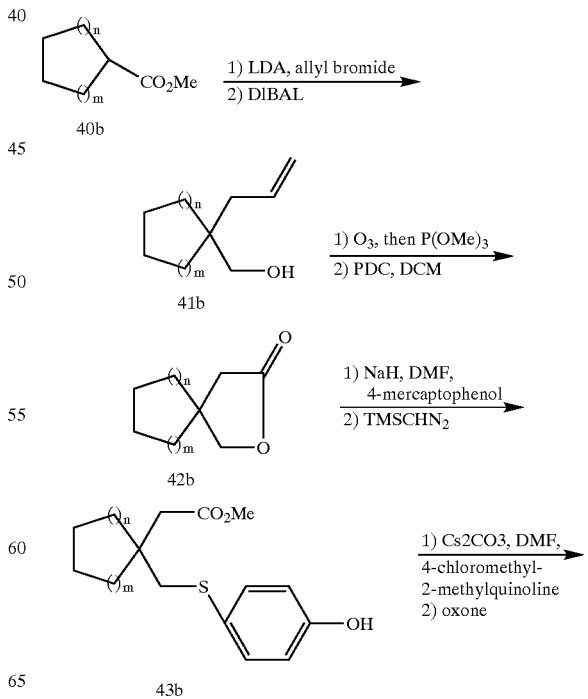

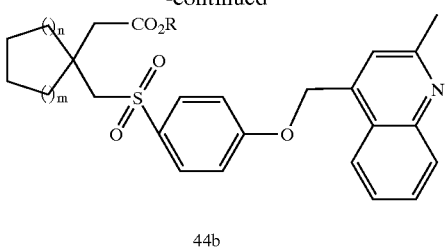

44b m = 0–3
n = 0–2
R = Me

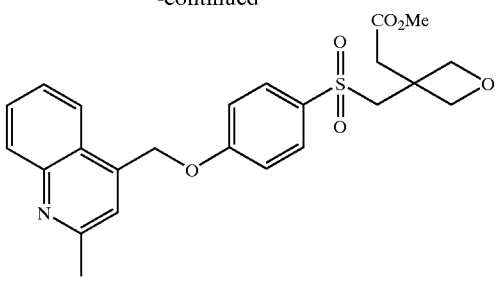

50

The synthesis of 4-membered oxygen-containing heterocycle 50 commences from dimethyl allylmalonate 45. LDA deprotonation, followed by addition of BOMCl, furnishes a quaternary center on the α-position of the carbonyl groups. LAH reduction results in diol 46, which is converted to its mono-toluenesulfonate 47 in one step. The mono-toluenesulfonate 47 is subjected to the action of NaH/THF, under which conditions formation of oxetane 48 is realized. Manipulation of allyl group to ester function in 48 can be achieved without any complication and the benzyl group is removed under Pd/C condition in the atmosphere of hydrogen to provide intermediate 49. Following the chemistry analogous to that described in scheme 10, the final compound 50 can be easily prepared from intermediate 49 in four steps.

Scheme 12

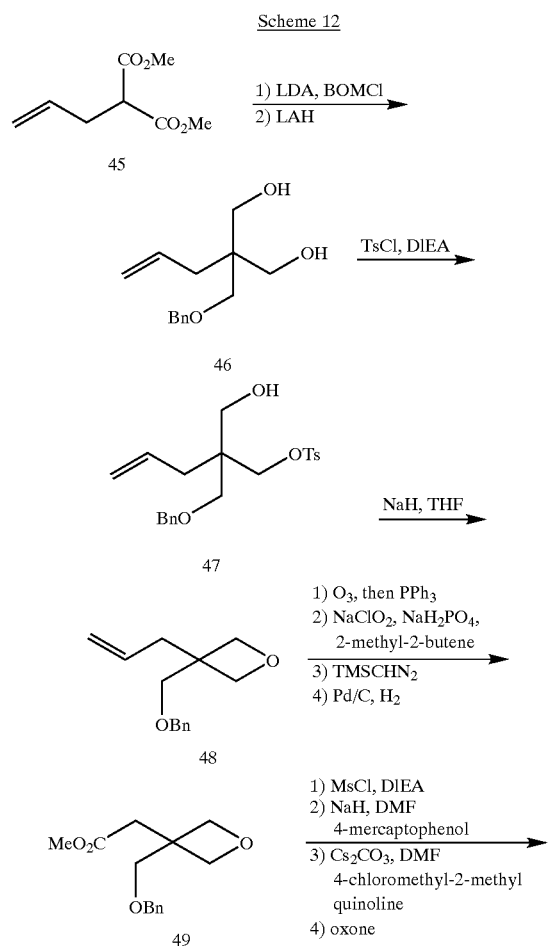

Lactam-based compound 54 can be made using chemistry similar to that described in scheme 10. LDA promoted alkylation allows the introduction of an allyl group at the α-position of the lactam function in 51 (see scheme 13). Aldol condensation with paraformaldehyde mediated by LDA furnishes the desired quaternary carbon center in 53. By employing the chemistry analogous to that described in scheme 10, the final compound 54 can be produced without any complication.

Scheme 13

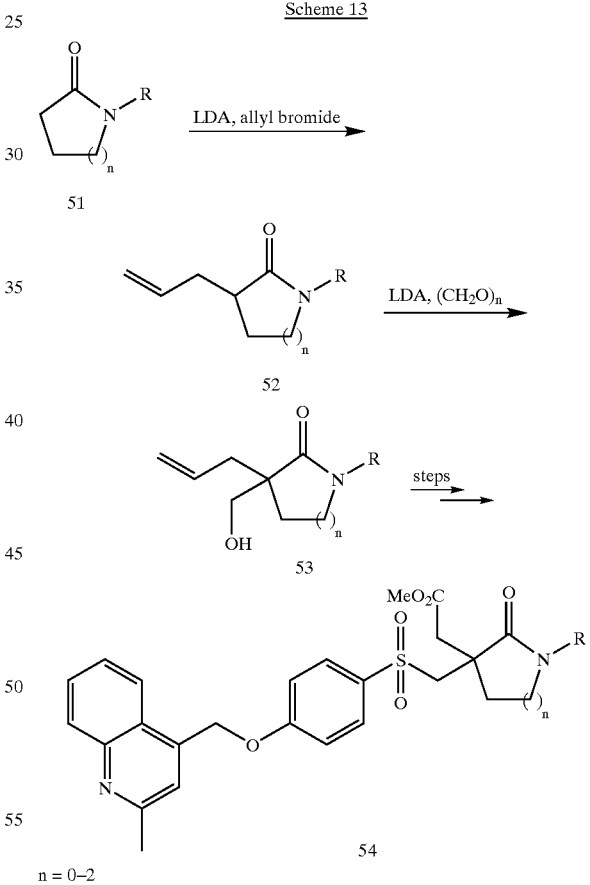

n = 0–2

Dihydro-isooxazoline compound 58 is made through the route outlined in scheme 14. Itaconic acid monobutyl ester 55 is chemoselectively converted to allylic alcohol 56 through a mixed anhydride intermediate. The dihydro-isooxazoline core structure 57 can be constructed via a [3+2] cycloaddition approach. Once the core structure is built up, the rest of the chemical transformations are almost the same as those outlined in scheme 9.

Scheme 14

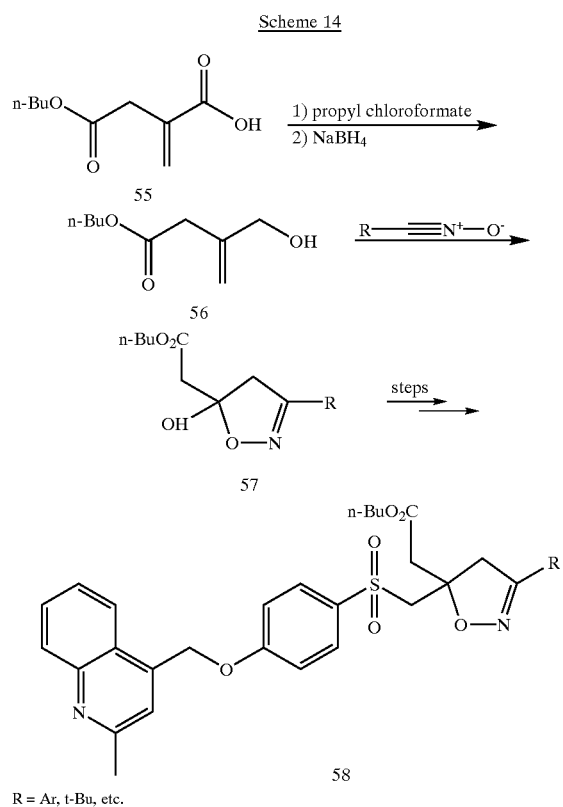

R = Ar, t-Bu, etc.

see Scheme 9 for more details about these steps

One enantiomer or diastereomer of a compound of Formula I may display superior activity compared with the others. Thus, the following stereochemistries are considered to be a part of the present invention.

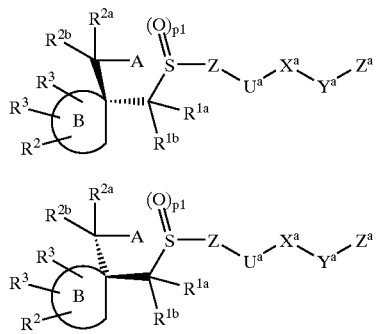

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tetr. Lett.* 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α" and "β" are stereochemical designations familiar to those skilled in the art.

Example 1

N-hydroxy-2-{2-[({4-[(2-methyl-4-quinolinyl)methoxy]phenyl}sulfonyl)methyl]-2-pyrrolidinyl}acetamide bis(trifluoroacetate)

(1a) To a solution of N-Boc-proline (25.0 g, 116 mmol) in acetone (800 mL) were added potassium carbonate (80.3 g, 581 mmol, 5 eq.) and iodomethane (82.5 g, 581 mmol) at room temperature. The mixture was stirred overnight. After filtration over Celite®, the filtrate was concentrated under reduced pressure. The residue was dissolved in ethyl acetate and it was washed with water and brine. The organic layer was dried over MgSO$_4$. After removing the solvent, the crude material (24.9 g, 94% yield) was identified as N-Boc-proline methyl ester and was pure enough for the next reaction. MS found: 230 (M+1).

(1b) To a freshly prepared LDA solution (~1.0 M, 82 mmol) at −78° C. was added a solution of the methyl ester (1a) (15.5 g, 68 mmol) in 200 mL of anhydrous THF. The mixture stirred at −78° C. for 1 h and then a solution of allyl bromide (6.5 mL, 74 mmol) in 20 mL of anhydrous THF was added. The reaction mixture was gradually warmed to room temperature over 1.5 h. TLC revealed no more starting material left and the solvent was directly removed under reduced pressure. The residue was digested in 10% ether in hexane and the solution was filtered over a short pad of silica gel. The pad was washed with 10–15% of ether in hexane. After removal of the solvent from the combined organic layers, the desired product (16.5 g, 91% yield) was obtained and was pure enough for next reaction based on $^1$H NMR evidence.

(1c) To a solution of the allylated compound (1b) (6.0 g, 22 mmol) in 200 mL of C$_2$Cl$_2$ at −78° C. was added a solution of DIBAL in toluene (1.5 M, 67 mmol, 45 mL). The mixture was warmed up to room temperature over 12 h and TLC detected no starting material in solution. The excess DIBAL was quenched with 5.0 mL of MeOH, followed by the addition of 5.0 mL of H$_2$O. The suspension was stirred for 15 min before a large excess amount of Na$_2$SO$_4$ was added. After the addition of Na$_2$SO$_4$, the supernatant was stirred for 1 h before it was filtered over silica gel. The pad of white solid was washed several times with ether. The solvent of the filtrate was removed under reduced pressure and the desired alcohol (4.2 g, 78% yield) was obtained. This material was pure enough for the next reaction. MS found: 242 (M+1).

(1d) To a solution of the alcohol (1c) (4.1 g, 17 mmol) in 100 mL of C$_2$Cl$_2$ at −20° C. were added DIEA (85 mmol, 15 mL, 5 eq.) and MsCl (51 mmol, 4.0 mL, 3 eq.). The mixture was gradually warmed up to room temperature and stirred for 2 h. TLC revealed no starting material left in solution and it was poured into ice water. The aqueous layer was extracted with ethyl acetate (200 mL×2) and the combined organic phase was washed with H₂O and brine. After dried over MgSO₄ and filtered, the solvent was removed under reduced pressure. The residue was purified on SiO₂ column using 30–40% ether in hexane and the desired mesylate was obtained (5.20 g, 96% yield). MS found: 320 (M+1).

(1e) To a solution of 4-mercaptophenol (4.1 g, 32 mmol) in 20 mL of anhydrous DMF at 0° C. was added NaH (2.0 g, 60%, 49 mmol) in one portion. The yellowish solution was allowed to stir for 20 min before a solution of the mesylate (1d) (5.2 g, 16 mmol) in 20 mL of DMF was added. The mixture stirred for 2 days and then was heated to 80° C. for 2 h. The solution was filtered and neutralized. After removal of the solvent under vacuum, the residue was directly purified on SiO₂ column chromatography using 30% ether in hexane. The desired sulfide was obtained (4.0 g, 70% yield). MS found: 350 (M+1).

(1f) To a solution of the sulphide (1e) (2.5 g, 7.1 mmol) in 20 mL of anhydrous DMF at room temperature were added tetrabutylammonium iodide (TBAI) (0.26 g, 0.1 eq.), K₂CO₃ (3.0 g, 21.5 mmol, 3 eq.), and 4-chloromethyl-2-methylquinoline hydrochloric acid (1.96 g, 8.6 mmol). The mixture stirred at room temperature for 12 h. TLC revealed no starting material left and the suspension was diluted with ether. The etherate was filtered over a short pad of silica gel and the pad was washed with ether several times. The combined filtrates were evaporated under vacuum and the residue was purified via column chromatography using 30% ether in hexane. The desired coupling product was isolated (3.3 g, 91% yield). MS found: 505 (M+1).

(1g) Oxone® (8.8 g, 14 mmol) was dissolved in 70 mL of H₂O and the pH of the solution was adjusted to 3 using a Na₂CO₃ solution. In another flask, the coupling product from reaction (1f) (3.3 g, 6.5 mmol) was dissolved in a mixture of 20 mL of THF and 50 mL of MeOH. The Oxone® solution was added to it and the mixture was allowed to stir for 2 h. The pH of the solution was adjusted to 10 using Na₂CO₃ and the aqueous solution was extracted with ethyl acetate (150 mL×2). The combined organic phases were washed with brine and dried over MgSO₄. After evaporation of the solvent, the residue was purified via column chromatography using 10% ether in hexane and the sulfone product was obtained (1.4 g, 40% yield). MS found: 537 (M+1).

(1h) To a solution of the sulfone derivative (1g) (1.4 g, 2.6 mmol) in 150 mL of CH₂Cl₂ at −78° C. was bubbled a flow of ozone for 10 min until the solution turned to blue. PPh₃ (3.5 g, 13 mmol) was then added and the mixture was warmed to room temperature over 12 h. The solvent was removed and the residue was purified via column chromatography using 40–50% ethyl acetate. The desired aldehyde was obtained and the product was contaminated with triphenylphosphine oxide. MS found: 539 (M+1).

(1i) To a solution of the aldehyde (1h) (~2.6 mmol) in 5 mL of t-BuOH at room temperature were added 2-methyl-2-butene (4.2 mL, 40 mmol) and a solution of NaClO₂ (1.1 g, 12 mmol), and NaH₂PO₄ (0.72 g, 6 mmol) in 4.0 mL of H₂O. The mixture stirred for 2 h until the disappearance of starting material. The solvent was removed under vacuum and the aqueous solution was diluted with 10 mL of H₂O. The pH of the solution was adjusted to 7 using 1M HCl. The aqueous layer was extracted with CH₂Cl₂ (100 mL×4). The combined organic phase was washed once with brine and dried over MgSO₄. After filtration, followed by evaporation of the solvent, the residue thus obtained was purified via column chromatography using 5–10% MeOH in CH₂Cl₂. The desired carboxylic acid was obtained (0.75 g, 52% yield for two steps). MS found: 555 (M+1).

(1j) To a solution of the carboxylic acid (1i) (0.75 g, 1.35 mmol) in a mixture of 10 mL of MeOH and 10 mL of benzene was added a solution of TMSCHN₂ (2.0 M in hexane) until the solution turned to yellow. The excess reagent was quenched with 2 drops of acetic acid and the solution was concentrated under reduced pressure. The residue (0.75 g, quantitative yield) thus obtained was pure enough for next reaction. MS found: 569 (M+1).

(1k) To a solution of the methyl ester (1j) (0.75 g, 1.35 mmol) in 2 mL of C₂Cl₂ at room temperature was added TFA (2.0 mL). The mixture stirred for 3 h before the solvent was removed. The residue thus obtained (>1.0 g, quantitative yield) was pure enough for the next reaction. MS found: 469 (M+1).

(1l) To a flask containing the material (60 mg, 0.086 mmol) obtained from (1k) was added a solution of NH₂OH/KOH/MeOH (1.76M, 2.0 mL) at room temperature. The mixture was stirred for 30 min and then quenched with conc. HCl to pH=7. After evaporation of MeOH, the residue was purified via HPLC and the final hydroxamic acid was obtained (40 mg, 66% yield). MS found: 470 (M+1).

Example 2

N-hydroxy-2-{1-methyl-2-[({4-[(2-methyl-4-quinolinyl)methoxy]phenyl}sulfonyl)methyl]-2-pyrrolidinyl}acetamide bis(trifluoroacetate)

(2a) To a solution of the pyrrolidine derivative (1k) (70 mg, 0.10 mmol) in 2 mL of DMF were added DIEA (0.35 mL, 2.0 mmol), formaldehyde solution (37% in H₂O, 0.1 mL, 1.0 mmol) and NaBH(OAc)₃ (85 mg, 0.4 mmol). The mixture stirred overnight and the solution was directly subject to HPLC purification. The desired N-methylated product was obtained (50 mg, 71% yield). MS found: 483 (M+1).

(2b) Following a procedure analogous to that used in reaction (1l), the N-methylated compound (50 mg, 0.07 mmol) from (2a) was reacted with 2.0 mL of NH₂OH/KOH/MeOH. The desired hydroxamic acid was isolated via HPLC (30 mg, 60% yield). MS found: 484 (M+1).

Example 3

N-hydroxy-2-{1-isobutyl-2-[({4-[(2-methyl-4-quinolinyl)methoxylphenyl}sulfonyl)methyl]-2-pyrrolidinyl}acetamide bis(trifluoroacetate)

(3a) To a solution of the pyrrolidine derivative (1k) (70 mg, 0.10 mmol) in 2 mL of DMF were added DIEA (0.35 mL, 2.0 mmol), isobutyraldehyde (0.1 mL, 1.0 mmol) and NaBH(OAc)₃ (100 mg, 0.5 mmol). The mixture stirred overnight and the solution was directly subject to HPLC purification. The desired N-isobutylated product was obtained (50 mg, 71% yield). MS found: 525 (M+1).

(3b) Following a procedure analogous to that used in reaction (1l), the N-isobutylated compound (50 mg, 0.07 mmol) from (3a) was reacted with 2.0 mL of NH₂OH/KOH/MeOH. The desired hydroxamic acid was isolated via HPLC (28 mg, 50% yield). MS found: 526 (M+1).

Example 4

N-hydroxy-2-[2-[({4-[(2-methyl-4-quinolinyl)methoxy]phenyl}sulfonyl)methyl]-1-(3-pyridinyl)-2-pyrrolidinyl}acetamide tris(trifluoroacetate)

(4a) To a solution of the pyrrolidine derivative (1k) (70 mg, 0.10 mmol) in 2 mL of DMF were added DIEA (0.35 mL, 2.0 mmol), 3-pyridinecarboxaldehyde (0.1 mL, 1.0 mmol) and NaBH(OAc)$_3$ (100 mg, 0.5 mmol). The mixture stirred overnight and the solution was directly subject to HPLC purification. The desired N-alkylated product was obtained (70 mg, 78% yield). MS found: 560 (M+1).

(4b) Following a procedure analogous to that used in reaction (1l), the N-alkylated compound (70 mg, 0.078 mmol) from (4a) was reacted with 5.0 mL of NH$_2$OH/KOH/MeOH. The desired hydroxamic acid was isolated via HPLC (40 mg, 58% yield). MS found: 561 (M+1).

Example 5

2-{1-acetyl-2-[({4-[(2-methyl-4-quinolinyl)methoxy]phenyl}sulfonyl)methyl]-2-pyrrolidinyl}-N-hydroxyacetamide trifluoroacetate (5a) To a solution of the pyrrolidine derivative (1k) (90 mg, 0.13 mmol) in 3 mL of CH$_2$Cl$_2$ were added TEA (0.07 mL, 0.52 mmol) and acetic anhydride (0.025 mL, 0.26 mmol). The mixture stirred overnight and the solvent was removed under reduced pressure. The residue was purified via column chromatography using 1–2% MeOH in CH$_2$Cl$_2$. The desired N-acetyl product was isolated (65 mg, >95% yield). MS found: 511 (M+1).

(5b) Following a procedure analogous to that used in reaction (1l), the N-acetyl product (65 mg, 0.13 mmol) from (5a) was reacted with 5.0 mL of NH$_2$OH/KOH/MeOH. The desired hydroxamic acid was isolated via HPLC (40 mg, 50% yield). MS found: 512 (M+1).

Example 6

N-hydroxy-2-{3-[({4-{(2-methyl-4-quinolinyl)methoxy]phenyl}sulfonyl)methyl]-3-pyrrolidinyl}acetamide bis(trifluoroacetate)

(6a) To a solution of t-butyl-3-oxo-1-pyrrolidinecarboxylate (5.0 g, 27 mmol) in 200 mL of anhydrous toluene was added methyl (triphenylphosphoranylidene)acetate (13.5 g, 40.5 mmol, 1.5 eq.) at room temperate. The mixture was refluxed overnight and TLC showed disappearance of starting material. The mixture was filtered through a pad of silica gel and the pad was washed with 20% of ethyl acetate in hexane. After removal of the solvent from the filtrate, the residue (5.9 g, 91% yield) was obtained as a mixture of regioisomers, which was pure enough for the next reaction.

(6b) To a solution of the α, β-unsaturated ester (5.7 g, 23.6 mmol) from (6a) in 100 mL of C$_2$Cl$_2$ at −78° C. was added DIBAL solution (1.0M in CH$_2$Cl$_2$, 90 mL). The mixture stirred at −78° C. for 1 h and TLC showed disappearance of starting material. The reaction was quenched with 5 mL of MeOH, followed by 5 mL of H$_2$O. After the solution was warmed to room temperature, 30 g of Na$_2$SO$_4$ was added it. The supernatant was allowed to stir vigorously for 2 h and then it was filtered through a pad of silica gel. The pad was washed with ethyl acetate and the filtrate was concentrated under vacuum. The residue (5.0 g, >95% yield) was obtained as a mixture of regioisomers. MS found: 214 (M+1).

(6c) To a solution of the material from (6b) (5.0 g, 23.5 mmol) in 20 mL of triethyl orthoacetate was added a catalytic amount of propionic acid (0.02 mL). The mixture was degassed and subsequently sealed. The seal tube was immersed into an oil bath and heated to 180° C. for 2 days until TLC showed disappearance of starting material. The solvent was removed and the residue was purified via column chromatography using 15% of ethyl acetate in hexane as eluent. The desired product was obtained (3.85 g, 58% yield). MS found: 284 (M+1).

(6d) To a solution of the material from (6c) (3.85 g, 13.6 mmol) in 100 mL of C$_2$Cl$_2$ at −78° C. was bubbled a flow of ozone until the color of the solution turned to blue. The excess ozone was blown off under N$_2$ and then trimethyl phosphite (3.2 mL, 27.2 mmol, 2 eq.) was added to it. The mixture was allowed to stir overnight. After aqueous work-up and removal of the solvent, the residue was purified via column chromatography to provide the aldehyde (1.64 g, 42%). MS found: 286 (M+1).

(6e) To a solution of the aldehyde from (6d) (1.64 g, 5.8 mmol) in 10 mL of MeOH at 0° C. added 0.22 g of NaBH$_4$ (5.8 mmol). The mixture stirred at room temperature overnight. After aqueous work-up, the residue was purified via column chromatography using 40% of ethyl acetate in hexane as eluent. The desired alcohol was obtained (1.01 g, 61% yield). MS found: 288 (M+1).

(6f) To a solution of the alcohol from reaction (6e) (1.0 g, 3.5 mmol) in 30 mL of CH$_2$Cl$_2$ at 0° C. were added DIEA (1.2 mL, 7.0 mmol) and methanesulfonyl chloride (0.32 mL, 4.2 mmol). The reaction mixture was stirred at room temperature overnight and TLC showed disappearance of starting material at that point. The mixture was diluted with ethyl acetate, washed with H$_2$O and brine, and dried over MgSO$_4$. The solvent was stripped off after filtration and the residue was purified by column chromatography using 35% of ethyl acetate in hexane as eluent. The desired product was obtained (0.82 g, 64% yield). MS found: 366 (M+1).

(6g) To a suspension of NaH (0.27 g, 6.7 mmol) in 5.0 mL of DMF at 0° C. was added 4-mercaptophenol (0.71 g, 5.6 mmol). The yellowish solution was allowed to stir for 30 min before a solution of the mesylate from reaction (6f) (0.82 g, 2.2 mmol) in 5 mL of DMF was added to it. The mixture stirred overnight and TLC showed disappearance of the mesylate. The reaction was quenched with 1 mL of H$_2$O and diluted with ethyl acetate. The organic phase was washed with H$_2$O and brine, and dried over MgSO$_4$. After filtration, the solvent was stripped off and the residue was purified by column chromatography using 35% of ethyl acetate in hexane as eluent. The desired product was obtained (0.5 g, 57% yield). MS found: 396 (M+1).

(6h) To a solution of the material from (6g) (0.51 g, 1.3 mmol) in 5 mL of DMF at room temperature were added TBAI (0.04 g, 1.3 mmol)), Cs$_2$CO$_3$ (0.68 g, 5.8 mmol), and 4-chloromethyl-2-methylquinoline hydrochloric acid (0.30 g, 1.5 mmol). The mixture was allowed to stir for 2 days until the starting material disappeared. The solid was filtered and the solvent of the filtrate was stripped off. The residue was purified by column chromatography using 60% of ethyl acetate in hexane as eluent. The desired product was isolated in 94% yield (0.67 g). MS found: 551 (M+1).

(6i) To a solution of the material from reaction (6h) (0.66 g, 1.2 mmol) in 5 mL of MeOH at 0° C. was added a solution of Oxone® (1.47 g, 6.2 mmol) in 4 mL of H$_2$O dropwise. The reaction mixture stirred at room temperature until the starting material disappeared. The mixture was taken into 200 mL of ethyl acetate and washed with H$_2$O and brine, and dried over MgSO$_4$. After filtration, the solvent was stripped off and the product was obtained without further purification (0.60 g, 86% yield). MS found: 583 (M+1).

(6j) To a solution of the sulfone derivative from reaction (6i) (50 mg, 0.08 mmol) in 2 mL of CH$_2$Cl$_2$ at room temperature was added 2.0 mL of TFA. The reaction mixture stirred for 2 h. After removal the reagent under vacuum, the residue was taken for the next reaction.

To a flask containing the residue from the BOC deprotection reaction was added a solution of NH$_2$OH/KOH/MeOH (1.76M, 5.0 mL, 8.5 mmol, 100 eq.) at room temperature. The solution stirred for 40 min until the starting material disappeared. The reaction was quenched with concentrated HCl and the solid formed was removed through filtration. Methanol was evaporated under vacuum and the residue was purified via HPLC to provide the desired product (50 mg, 80% yield). MS found: 470 (M+1).

Example 7

N-hydroxy-2-{1-methyl-3-[({4-{(2-methyl-4-quinolinyl)methoxy]phenyl}sulfonyl)methyl]-3-pyrrolidinyl}acetamide bis(trifluoroacetate)

(7a) To a solution of the sulfone derivative from reaction (6i) (38 mg, 0.065 mmol) in 2 mL of CH$_2$Cl$_2$ at room temperature was added 2 mL of TFA. The reaction mixture stirred for 2 h. After removal the reagent under vacuum, the residue was taken for the next reaction. To a solution of the material prepared above in 2.0 mL of DMF at room temperature were added DIEA (0.34 mL, 1.9 mmol), 30% formaldehyde (0.05 mL, 0.65 mmol), and NaBH(OAc)$_3$ (70 mg, 0.33 mmol). The mixture stirred for 1 h and was directly purified via HPLC. The desired product was isolated as TFA salt (45 mg, >95% yield). MS found: 497 (M+1).

(7b) To a flask containing the material from reaction (7a) (45 mg, 0.062 mmol) at room temperature was added a solution of NH$_2$OH/KOH/MeOH (1.76M, 5 mL). The solution stirred for 1 h before it was quenched with concentrated HCl. The solid form was removed and the filtrate was concentrated. The residue was purified via HPLC to provide the desired product (40 mg, 90% yield). MS found: 484 (M+1).

Example 8

N-hydroxy-2-{1-isopropyl-3-[({4-{(2-methyl-4-quinolinyl)methoxy]phenyl}sulfonyl)methyl]-3-pyrrolidinyl}acetamide bis(trifluoroacetate)

(8a) To a solution of the sulfone derivative from reaction (6i) (50 mg, 0.085 mmol) in 2 mL of CH$_2$Cl$_2$ at room temperature was added 2 mL of TFA. The reaction mixture stirred for 2 h. After removal the reagent under vacuum, the residue was taken for the next reaction. To a solution of the material prepared above in 2.0 mL of DMF at room temperature were added DIEA (0.45 mL, 2.5 mmol), acetone (0.05 mL, 0.85 mmol), and NaBH(OAc)$_3$ (89 mg, 0.42 mmol). The mixture stirred overnight and was directly purified via HPLC. The desired product was isolated as TFA salt (55 mg, 86% yield). MS found: 525 (M+1).

(8b) Following a procedure analogous to that used in reaction (7b), the N-isopropylated compound (55 mg) was treated with 4 mL of a solution of NH$_2$OH/KOH/MeOH (1.76M) at room temperature for 1 h. The reaction was quenched with concentrated HCl and the solid formed was filtered. After concentration of the filtrate, the residue was directly purified via HPLC to provide the desired product (40 mg, 73% yield). MS found: 512 (M+1).

Example 9

N-hydroxy-2-{1-isobutyl-3-[({4-{(2-methyl-4-quinolinyl)methoxy]phenyl}sulfonyl)methyl]-3-pyrrolidinyl}acetamide bis(trifluoroacetate)

(9a) Following a procedure analogous to that used in reaction (8a), 100 mg of the deprotection product (0.14 mmol) from TFA reaction was dissolved in 3 mL of DMF. To this solution were added DIEA (0.5 mL, 2.8 mmol), isobutyraldehyde (0.12 mL, 1.4 mmol), and NaBH(OAc)$_3$ (148 mg, 0.70 mmol). The reaction mixture stirred at room temperature for 2 h and it was directly purified via HPLC to provide the desired product (80 mg, 74% yield). MS found: 539 (M+1).

(9b) Following a procedure analogous to that used in reaction (7b), the N-isobutylated compound (80 mg) was treated with 4 mL of a solution of NH$_2$OH/KOH/MeOH (1.76M) at room temperature for 1 h. The reaction was quenched with concentrated HCl and the solid formed was filtered. After concentration of the filtrate, the residue was directly purified via HPLC to provide the desired product (60 mg, 75% yield). MS found: 526 (M+1).

Example 10

N-hydroxy-2-{3-[({4-{(2-methyl-4-quinolinyl)methoxy]phenyl}sulfonyl)methyl]-1-neopentyl-3-pyrrolidinyl}acetamide bis(trifluoroacetate)

(10a) Following a procedure analogous to that used in reaction (8a), 100 mg of the deprotection product (0.14 mmol) from TFA reaction was dissolved in 3 mL of DMF. To this solution were added DIEA (0.5 mL, 2.8 mmol), trimethyl-acetaldehyde (0.15 mL, 1.4 mmol), and NaBH (OAc)$_3$ (148 mg, 0.70 mmol). The reaction mixture stirred at room temperature for 2 h and it was directly purified via HPLC to provide the desired product (60 mg, 55% yield). MS found: 553 (M+1).

(10b) Following a procedure analogous to that used in reaction (7b), the N-neopentylated compound (60 mg) was treated with 4 mL of a solution of NH$_2$OH/KOH/MeOH (1.76M) at room temperature for 1 h. The reaction was quenched with concentrated HCl and the solid formed was filtered. After concentration of the filtrate, the residue was directly purified via HPLC to provide the desired product (45 mg, 75% yield). MS found: 540 (M+1).

Example 11

N-hydroxy-2-{2-[({4-[(2-methyl-4-quinolinyl)methoxy]phenyl}sulfonyl)methyl]-2-piperidinyl}acetamide bis(trifluoroacetate)

(11a) To freshly prepared LDA (1M in THF, 187 mL) at −78° C. was added a solution of 1-tert-butyl-2-methyl-1,2-piperidinedicarboxylate (32.4 g, 133 mmol) in 300 mL of anhydrous THF. The reaction mixture stirred for 30 min at −78° C. and then warmed to room temperature for 30 min. The mixture was cooled down to −78° C. and a solution of allyl bromide (13.8 mL, 160 mmol) in 20 mL of THF was added to it. The mixture was warmed to room temperature and stirred overnight. The solvent was removed under reduced pressure and the residue was digested in ether/hexane. The suspension was passed through a pad of silica gel and washed with a mixture of ether and hexane. The filtrate was concentrated and the desired product was obtained without further purification (30.3 g, 81%). MS found: 284 (M+1).

(11b) To a solution of the material from reaction (11a) (30.3 g, 107 mmol) in 400 mL of C$_2$Cl$_2$ at −78° C. was added DIBAL (1.5M in toluene, 214 mL, 321 mmol). The reaction mixture stirred for 45 min and then was warmed to room temperature for another 45 min. The reaction was quenched by addition of 50 mL of MeOH, followed by addition of 50 mL of H$_2$O. Finally, to this supernatant was added 130 g of NaOAc and the mixture stirred for 45 min. The mixture was passed through a pad of Celite® and the solid was washed with ethyl acetate. The solvent of the filtrate was stripped off and the product was obtained without further purification (18 g, 66% yield). The product isolated was a cyclic urethane resulting from cyclization between the alcohol and Boc group. MS found: 363 (2M+1).

(11c) To a solution of 4-mercaptophenol (1.3 g, 10.2 mmol) in 10 mL of DMF at 0° C. was added NaH (0.63 g, 60%, 15.3 mmol). The suspension stirred for 30 min. To it was added a solution of the material from reaction (11b) (1.0 g, 5.3 mmol) in 5 mL of DMF. The reaction mixture stirred overnight before it was filtered. The solvent was removed under reduced pressure. The residue was directly loaded on $SiO_2$ column and purified using 5% MeOH in $CH_2Cl_2$. The desired product was obtained in 75% yield. MS found: 266 (M+1).

(11d) To a solution of material from reaction (11c) (3.0 g, 11.4 mmol) in 25 mL of DMF was added $Cs_2CO_3$ (11.0 g, 34.0 mmol), TBAI (0.5 g, 1.36 mmol) and 4-chloromethyl-2-methylquinoline hydrochloric acid (2.6 g, 11.4 mmol). The mixture was stirred overnight before the solid was filtered off. The solvent was then removed under reduced pressure and the residue was purified by column chromatography using 5% MeOH in $C_2Cl_2$ as eluent. The desired product was isolated in 80% yield (3.8 g). MS found: 419 (M+1).

(11e) To a solution of material from reaction (11d) (3.8 g, 9.0 mmol) in 100 mL of $C_2Cl_2$ at room temperature were added DIEA (3.1 mL, 18 mmol) and $(Boc)_2O$ (3.0 g, 13.6 mmol). The mixture stirred until the starting material disappeared. The solvent was removed and the residue was purified by column chromatography to provide the desired product (3.6 g, 77% yield). MS found: 519 (M+1).

(11f) Following a procedure analogous to that used in reaction (1g), the material from reaction (11e) (3.5 g, 6.8 mmol) was oxidized to the sulfone derivative in 96% yield (3.6 g). MS found: 551 (M+1).

(11g) Following a procedure analogous to that used in reaction (1h), the material from reaction (11e) (3.6 g, 6.5 mmol) was ozonolyzed to provide the corresponding aldehyde (0.5 g, 14% yield). MS found: 553 (M+1).

(11h) Following a procedure analogous to that used in reaction (1i), the aldehyde from reaction (11g) (0.5 g, 0.9 mmol) was oxidized to provide the corresponding carboxylic acid (0.5 g, >95% yield). MS found: 569 (M+1).

(11i) To a solution of the acid from reaction (11h) (0.5 g, 0.9 mmol) in 40 mL of MeOH at −78° C. was bubbled a flow of HCl until it was saturated. The solution was warmed to room temperature overnight. The solvent was removed under reduced pressure and the desired material was obtained as HCl salt (0.54 g, >95% yield). MS found: 483 (M+1).

(11j) To a flask containing the material from reaction (11i) (60 mg, 0.08 mmol) was added a solution of $NH_2OH/KOH/MeOH$ at room temperature. The solution stirred for 45 min before it was quenched with concentrated HCl. The solution was concentrated and the solid precipitated from the solution was removed by filtration. The filtrate was directly loaded on HPLC and the desired product was obtained (42 mg, 70% yield). MS found: 484 (M+1).

Example 12

N-hydroxy-2-{1-methyl-2-[({4-[(2-methyl-4-quinolinyl)methoxy]phenyl}sulfonyl)methyl]-2-piperidinyl}acetamide bis(trifluoroacetate)

(12a) Following a procedure analogous to that used in reaction (7a), the material from reaction (11i) (60 mg, 0.11 mmol) was converted to N-methylated derivative (45 mg, 57% yield). MS found: 497 (M+1).

(12b) Following a procedure analogous to that used in reaction (11j), the material from reaction (12a) (45 mg) was converted to the corresponding hydroxamic acid (30 mg, 67% yield). MS found: 498 (M+1).

Example 13

N-hydroxy-2-{1-isobutyl-2-[({4-[(2-methyl-4-quinolinyl)methoxy]phenyl}sulfonyl)methyl]-2-piperidinyl}acetamide bis(trifluoroacetate)

(13a) Following a procedure analogous to that used in reaction (7a), the material from reaction (11i) (60 mg, 0.11 mmol) was converted to N-isobutylated derivative (43 mg, 52% yield). MS found: 539 (M+1).

(13b) Following a procedure analogous to that used in reaction (11j), the material from reaction (13a) (43 mg) was converted to the corresponding hydroxamic acid (18 mg, 42% yield). MS found: 540 (M+1).

Example 14

N-hydroxy-2-{3-[({4-[(2-methyl-4-quinolinyl)methoxy]phenyl}sulfinyl)methyl]-3-piperidinyl}acetamide bis(trifluoroacetate)

(14a) To a solution of ethyl nipecotate (10 g, 64 mmol) in 100 mL of $CH_2Cl_2$ at 0° C. were added DIEA (22 mL, 127 mmol) and $(Boc)_2O$ (21 g, 95 mmol). The mixture stirred until the starting material disappeared. The solvent was removed under reduced pressure and the residue was purified by column chromatography (25% ethyl acetate in hexane). The desired product was isolated (15.0 g, 91% yield). MS found: 258 (M+1).

(14b) Following a procedure analogous to that used in reaction (11a), the material from reaction (14a) (15.0 g, 58 mmol) was converted to the allylated product (8.6 g, 50% yield). MS found: 298 (M+1).

(14c) Following a procedure analogous to that used in reaction (11b), the material from reaction (14b) (8.6 g, 29 mmol) was transformed to the corresponding alcohol (5.9 g, 80% yield). MS found: 256 (M+1).

(14d) Following a procedure analogous to that used in reaction (1d), the alcohol from reaction (14c) (5.9 g, 23 mmol) was converted to the mesylate (3.5 g, 45% yield). MS found: 334 (M+1).

(14e) Following a procedure analogous to that used in reaction (1e), the mesylate from reaction (14d) (2.5 g, 7.4 mmol) was converted to corresponding sulphide (2.12 g, 80% yield). MS found: 364 (M+1).

(14f) Following a procedure analogous to that used in reaction (1f), the sulfide from reaction (14e) (2.1 g, 5.8 mmol) was alkylated with 4-chloromethyl-2-methylquinoline to provide the desired product (3.0 g, >95% yield). MS found: 519 (M+1).

(14g) Following a procedure analogous to that used in reaction (1h), the material from reaction (14f) (3.0 g, 5.8 mmol) was converted to the corresponding aldehyde while the sulfide function was also oxidized to the corresponding the sulphoxide. The product was isolated in large than 95% yield. MS found: 537 (M+1).

(14h) Following a procedure analogous to that used in reaction (1i), the aldehyde from reaction (14g) (3.0 g, 5.8 mmol) was converted to the corresponding carboxylic acid (3.0 g, >95% yield). MS found: 553 (M+1).

(14i) Following a procedure analogous to that used in reaction (1j), the acid (3.0 g, 5.8 mmol) was transformed to methyl eater (1.36, 41% yield). MS found: 567 (M+1).

(14j) Following a procedure analogous to that used in reaction (1k), the material from reaction (14i) (0.5 g, 0.9 mmol) was subjected to TFA and the Boc group was successfully removed to provide the product in quantitative yield. MS found: 467 (M+1).

(14k) Following a procedure analogous to that used in reaction (1l), the material from reaction (14j) (50 mg, 0.07 mmol) was converted to the corresponding hydroxamic acid (20 mg, 40% yield). MS found: 468 (M+1).

Example 15

N-hydroxy-2-{1-methyl-3-[({4-[(2-methyl-4-quinolinyl)methoxy]phenyl}sulfinyl)methyl]-3-piperidinyl}acetamide bis(trifluoroacetate)

(15a) Following a procedure analogous to that used in reaction (2a), the material from reaction (14j) (100 mg, 0.14 mmol) was converted to N-methylated product (60 mg, 60% yield). MS found: 481 (M+1).

(15b) Following a procedure analogous to that used in reaction (1l), the material from reaction (15a) (60 mg, 0.85 mmol) was converted to the corresponding hydroxamic acid (40 mg, 67% yield). MS found: 482 (M+1).

Example 16

N-hydroxy-2-{1-isopropyl-3-[({4-[(2-methyl-4-quinolinyl)methoxy]phenyl}sulfinyl)methyl]-3-piperidinyl}acetamide bis(trifluoroacetate)

(16a) Following a procedure analogous to that used in reaction (2a), the material from reaction (14j) (100 mg, 0.14 mmol) was converted to N-isopropylated product (70 mg, 68% yield). MS found: 509 (M+1).

(16b) Following a procedure analogous to that used in reaction (1l), the material from reaction (16a) (70 mg, 0.95 mmol) was converted to the corresponding hydroxamic acid (40 mg, 67% yield). MS found: 510 (M+1).

Example 17

N-hydroxy-2-{3-[({4-[(2-methyl-4-quinolinyl)methoxy]phenyl}sulfonyl)methyl]-3-piperidinyl}acetamide bis(trifluoroacetate)

(17a) Following a procedure analogous to that used in reaction (1g), the methyl ester from reaction (14i) (0.81 g, 1.43 mmol) was oxidized using Oxone® to provide the corresponding sulfone (0.42 g, 51% yield). MS found: 583 (M+1).

(17b) Following a procedure analogous to that used in reaction (1k), the Boc group of the material from reaction (17a) (0.42 g, 0.72 mmol) was removed under TFA conditions. The desired product was obtained in quantitative yield without purification. MS found: 483 (M+1).

(17c) Following a procedure analogous to that used in reaction (1l), the material from reaction (17b) (80 mg, 0.11 mmol) was converted to the corresponding hydroxamic acid (30 mg, 38% yield). MS found: 484 (M+1).

Example 18

N-hydroxy-2-{1-methyl-3-[({4-[(2-methyl-4-quinolinyl)methoxy]phenyl}sulfonyl)methyl]-3-piperidinyl}acetamide bis(trifluoroacetate)

(18a) Following a procedure analogous to that used in reaction (2a), the material from reaction (17b) (120 mg, 0.17 mmol) was converted to N-methylated product (100 mg, 82% yield). MS found: 497 (M+1).

(18b) Following a procedure analogous to that used in reaction (1l), the material from reaction (18a) (90 mg, 0.12 mmol) was converted to the corresponding hydroxamic acid (40 mg, 44% yield). MS found: 498 (M+1).

Example 19

N-hydroxy-2-{1-isopropyl-3-[({4-[(2-methyl-4-quinolinyl)methoxy]phenyl}sulfonyl)methyl]-3-piperidinyl}acetamide bis(trifluoroacetate)

(19a) Following a procedure analogous to that used in reaction (2a), the material from reaction (17b) (120 mg, 0.17 mmol) was converted using acetone to N-isopropylated product (80 mg, 63% yield). MS found: 525 (M+1).

(19b) Following a procedure analogous to that used in reaction (1l), the material from reaction (19a) (80 mg, 0.10 mmol) was converted to the corresponding hydroxamic acid (40 mg, 50% yield). MS found: 526 (M+1).

Example 20

N-hydroxy-2-{1-isobutyl-3-[({4-[(2-methyl-4-quinolinyl)methoxy]phenyl}sulfonyl)methyl]-3-piperidinyl}acetamide bis(trifluoroacetate)

(20a) Following a procedure analogous to that used in reaction (2a), the material from reaction (17b) (120 mg, 0.17 mmol) was converted using isobutyraldehyde to N-isobutylated product (80 mg, 62% yield). MS found: 539 (M+1).

(20b) Following a procedure analogous to that used in reaction (1l), the material from reaction (20a) (80 mg, 0.10 mmol) was converted to the corresponding hydroxamic acid (40 mg, 50% yield). MS found: 540 (M+1).

Example 21

N-hydroxy-2-{4-[({4-[(2-methyl-4-quinolinyl)methoxy]phenyl}sulfonyl)methyl]-4-piperidinyl}acetamide bis(trifluoroacetate)

(21a) Following a procedure analogous to that used in reaction (1a), 1-t-butoxycarbonyl-piperidine-4-carboxylic acid (10 g, 44 mmol) was converted to methyl ester (10.5 g) in quantitative yield. MS found: 244 (M+1).

(21b) Following a procedure analogous to that used in reaction (1b), the methyl ester from reaction (21a) (10.5 g, 43 mmol) was converted to the allylated product (12.3 g) in quantitative yield. MS found: 284 (M+1).

(21c) Following a procedure analogous to that used in reaction (1c), the allylated compound from reaction (21b) (10.5 g, 43 mmol) was reduced to the corresponding alcohol (8.7 g, 80% yield). MS found: 256 (M+1).

(21d) Following a procedure analogous to that used in reaction (1h), the material from reaction (21c) (6.6 g, 25.9 mmol) was converted to the corresponding aldehyde (1.0 g, 15% yield). MS found: 258 (M+1).

(21e) To a suspension of PDC (2.8 g, 7.8 mmol) in 100 mL of $C_2Cl_2$ at room temperature were added 4A MS(1.0 g) and a solution of the starting material from reaction (21d) (1.0 g, 3.9 mmol) in 20 mL of $CH_2Cl_2$. The mixture stirred overnight until all of the starting material was consumed. To the mixture were added 10 g of $SiO_2$ and the suspension stirred for 10 min before it filtered through a pad of Celite®. The pad was rinsed with $CH_2Cl_2$ and ethyl acetate. The solvent was removed under reduced pressure and the residue was purified by column chromatography to provide the desired lactone (0.71 g, 71% yield). MS found: 256 (M+1).

(21f) To a solution of 4-mercaptophenol (0.7 g, 5.56 mmol) in 5 mL of DMF at 0° C. was added NaH (0.20 g, 8.3 mmol). The yellowish solution was allowed to stir for 30 min before a solution of the material from reaction (21e) (0.71 g, 2.8 mmol) in 2 mL of DMF was added to it. The mixture was then heated to 140° C. overnight. DMF was removed under reduced pressure and the residue was taken into 50 mL of $H_2O$. The aqueous solution was extracted with ethyl acetate (35 mL×3) to remove the organic impurity and then the aqueous layer was acidified to pH=3. The aqueous layer was extracted with ethyl acetate (35 mL×3). The organic phase was washed with brine and dried over $MgSO_4$. The solvent was stripped off after filtration and the residue (1.05 g, >95% yield) was pure enough for the next reaction. MS found: 382 (M+1).

(21g) Following a procedure analogous to that used in reaction (1j), the material from reaction (21f) (1.05 g, 2.8 mmol) was converted to methyl ester (0.75 g, 67% yield). MS found: 396 (M+1).

(21h) Following a procedure analogous to that used in reaction (1f), the material from reaction (21g) (0.75 g, 1.9 mmol) was converted to the alkylation compound (0.87 g, 84% yield). MS found: 551 (M+1).

(21i) Following a procedure analogous to that used in reaction (1g), the material from reaction (21h) (0.87 g, 1.6 mmol) was converted to the sulfone derivative (0.68 g, 74% yield). MS found: 583 (M+1).

(21i) Following a procedure analogous to that used in reaction (1k), the material from reaction (21i) (0.68 g, 1.2 mmol) was converted to the product in quantitative yield. MS found: 483 (M+1).

(21k) Following a procedure analogous to that used in reaction (1l), the material from reaction (21j) (90 mg, 0.12 mmol) was converted to the corresponding hydroxamic acid (40 mg, 44% yield). MS found: 484 (M+1).

Example 22

N-hydroxy-2-{1-methyl-4-[({4-[(2-methyl-4-quinolinyl)methoxy]phenyl}sulfonyl)methyl]-4-piperidinyl}acetamide bis(trifluoroacetate)

(22a) Following a procedure analogous to that used in reaction (2a), the material from reaction (21j) (100 mg, 0.13 mmol) was converted to N-methylated product (100 mg, >95% yield). MS found: 497 (M+1).

(22b) Following a procedure analogous to that used in reaction (1l), the material from reaction (22a) (100 mg, 0.13 mmol) was converted to the corresponding hydroxamic acid (60 mg, 60% yield). MS found: 498 (M+1).

Example 23

N-hydroxy-2-{2-[({4-[(2-methyl-4-quinolinyl)methoxy]phenyl}sulfonyl)methyl]tetrahydro-2-furanyl}acetamide trifluoroacetate (23a) Following a procedure analogous to that used in reaction (1a), tetrahydro-2-furic acid (24.5 g, 210 mmol) was converted to the methyl ester (27.0 g, >95% yield). MS found: 131 (M+1).

(23b) Following a procedure analogous to that used in reaction (1b), the methyl ester from reaction (23a) (15.9 g, 122 mmol) was transformed to the allylation product (12.4 g, 60% yield). MS found: 171 (M+1).

(23c) Following a procedure analogous to that used in reaction (1c), the material from reaction (23b) (12.4 g, 73 mmol) was reduced to the corresponding alcohol (5.0 g, 48% yield). MS found: 143 (M+1).

(23d) Following a procedure analogous to that used in reaction (1d), the material from reaction (23c) (5.0 g, 35 mmol) was converted to the mesylate (6.9 g, 89% yield). MS found: 221 (M+1).

(23e) Following a procedure analogous to that used in reaction (1e), the mesylate from reaction (24d) (6.9 g, 31 mmol) was converted to the corresponding sulfide (3.5 g, 45% yield). MS found: 251 (M+1).

(23f) Following a procedure analogous to that used in reaction (1f), the sulfide from reaction (24e) (3.5 g, 14 mmol) was alkylated to provide the corresponding product (5.0 g, 88% yield). MS found: 406 (M+1).

(23g) Following a procedure analogous to that used in reaction (1g), the material from reaction (23f) (5.0 g, 12 mmol) was converted to the corresponding sulfone (5.1 g, 95% yield). MS found: 438 (M+1).

(23h) Following a procedure analogous to that used in reaction (1h), the material from reaction (23g) (5.1 g, 11.7 mmol) was converted to the aldehyde (2.2 g, 43% yield). MS found: 440 (M+1).

(23i) Following a procedure analogous to that used in reaction (1i), the aldehyde from reaction (23h) (2.2 g, 5 mmol) was oxidized to the corresponding acid (2.0 g, 83% yield). MS found: 456 (M+1).

(23j) Following a procedure analogous to that used in reaction (1j), the acid from reaction (23i) (2.0 g, 4.4 mmol) was converted to the methyl ester (1.1 g, 53% yield). MS found: 470 (M+1).

(23k) Following a procedure analogous to that used in reaction (1a), the material from reaction (23j) (100 mg, 0.21 mmol) was transformed to the corresponding hydroxamic acid (100 mg, 70% yield). MS found: 471 (M+1).

Example 24

N-hydroxy-2-{1-[({4-[(2-methyl-4-quinolinyl)methoxy]phenyl}sulfonyl)methyl]cyclobutyl}acetamide trifluoroacetate (24a) Following a procedure analogous to that used in reaction (1b), the ethyl cyclobutanecarboxylate (10 g, 78 mmol) was converted to the allylated product (12.5 g, 95% yield). MS found: 169 (M+1).

(24b) Following a procedure analogous to that used in reaction (1c), the material from reaction (24a) (12.5, 74 mmol) was reduced to the corresponding alcohol (7.7 g, 82% yield). MS found: 138 (M+1).

(24c) To a solution of the material from reaction (24b) (10.3 g, 82 mmol) in 300 mL of $C_2Cl_2$ was bubbled a flow of ozone until it turned to a blue solution. Trimethyl phosphite (20.4 g, 164 mmol) was added to it to reduce the ozonide overnight. After regular aqueous work-up and concentration, the residue was purified by column chromatography to provide the corresponding hemiacetal (4.6 g, 43% yield). MS found: 170 (M+1+$CH_3CN$).

(24d) To a suspension of PDC (9.5 g, 25 mmol) in 40 mL of $C_2Cl_2$ were added 4A MS and the material from reaction (24c) (1.6 g, 12.6 mmol). The mixture was stirred overnight until TLC showed disappearance of the starting material. The mixture was filtered through a short pad of silica gel and rinsed with ether. The solvent was removed under reduced pressure. The product was obtained without further purification (1.0 g, 64% yield). MS found: 168 (M+1+$CH_3CN$).

(24e) To a suspension of NaH (0.97 g, 60%, 24 mmol) in 30 mL of DMF were added 4-mercaptophenol (2.0 g, 16 mmol) and the material from reaction (24d) (1.1 g, 8 mmol). The mixture was heated to 140° C. overnight and the solvent was removed under reduced pressure. The residue was dissolved in water and the aqueous solution was extracted with ethyl acetate (30 mL×2). The aqueous solution was acidified to pH=2.0 using HCl (1.0M) and the aqueous solution was extracted with ethyl acetate (50 mL×3). The combined organic phase was dried over $MgSO_4$ and the product (1.8 g, 89% yield) was obtained after evaporation of the solvent. MS found: 503 (2M−1).

(24f) Following a procedure analogous to that used in reaction (1j), the material from reaction (24e) (1.8 g, 7.1 mmol) was converted to the corresponding methyl ester (1.52, 80% yield). MS found: 267 (M+1).

(24g) Following a procedure analogous to that used in reaction (1f), the material from reaction (24f) (1.65 g, 6.2 mmol) was converted to the alkylation product 1.84 g, 71% yield). MS found: 422 (M+1).

(24h) Following a procedure analogous to that used in reaction (1g), the material from reaction (24g) (1.0 g, 2.4 mmol) was converted to the corresponding sulfone (0.75 g, 70% yield). MS found: 454 (M+1).

(24i) Following a procedure analogous to that used in reaction (1l), the material from reaction (24h) (100 mg, 0.22 mmol) was converted to the corresponding hydroxamic acid (90 mg, 72% yield). MS found: 455 (M+1).

Example 25

N-hydroxy-2-{1-[({4-[(2-methyl-4-quinolinyl)methoxy]phenyl}sulfinyl)methyl]cyclobutyl}acetamide trifluoroacetate (25a) To a solution of the material from reaction (24g) (0.64 g, 1.5 mmol) in 5 mL of THF was added a solution of $NaIO_4$ in 5 mL of $H_2O$. The mixture was stirred overnight. After regular aqueous work-up and concentration, the residue was purified by column chromatography using 30% MeOH in $CH_2Cl_2$. The desired product (380 mg, 57% yield) was thus obtained. MS found: 438 (M+1).

(25b) Following a procedure analogous to that used in reaction (1l), the material from reaction (25a) (60 mg, 0.14 mmol) was converted to the corresponding hydroxamic acid (60 mg, 78% yield). MS found: 439 (M+1).

Example 26

N-hydroxy-2-{1-[({4-[(2-methyl-4-quinolinyl)methoxy]phenyl}sulfanyl)methyl]cyclobutyl}acetamide trifluoroacetate (26a) Following a procedure analogous to that used in reaction (1l), the material from reaction (24g) (120 mg, 0.28 mmol) was converted to the corresponding hydroxamic acid (140 mg, 93% yield). MS found: 423 (M+1).

Example 27

N-hydroxy-2-{1-[({4-[(2-methyl-4-quinolinyl)methoxy]phenyl}sulfonyl) methyl]cyclohexyl}acetamide trifluoroacetate (27a) Following a procedure analogous to that used in reaction (1b), the ethyl cyclohexanecarboxylate (7.0 g, 49 mmol) was converted to the allylation product (8.5 g, >95% yield). MS found: 182 (M+1).

(27b) Following a procedure analogous to that used in reaction (1c), the material from reaction (27a) (11.3 g, 62 mmol) was reduced to the corresponding alcohol (7.4 g, 78% yield). MS found: 196 (M+1+$CH_3CN$).

(27c) Following a procedure analogous to that used in reaction (25c), the material from reaction (27b) (5.4 g, 35 mmol) was converted to the corresponding hemiacetal (2.3 g, 46% yield). MS found: 156 (M).

(27d) Following a procedure analogous to that used in reaction (25d), the material from reaction (27c) (2.3 g, 15 mmol) was converted to the corresponding lactone (1.8 g, 78% yield). MS found: 309 (2M+1).

(27e) Following a procedure analogous to that used in reaction (25e), the material from reaction (27d) (1.8 g, 11 mmol) was converted to the corresponding sulfide (3.1 g, >95% yield). MS found: 559 (2M−1).

(27f) Following a procedure analogous to that used in reaction (1j), the material from reaction (27e) (2.0 g, 7.1 mmol) was converted to the corresponding methyl ester (1.57 g, 75% yield). MS found: 295 (M+1).

(27g) Following a procedure analogous to that used in reaction (1f), the material from reaction (27f) (1.57 g, 5.3 mmol) was converted to the alkylation product (1.94 g, 81% yield). MS found: 450 (M+1).

(27h) Following a procedure analogous to that used in reaction (1g), the material from reaction (27g) (0.5 g, 1.0 mmol) was converted to the corresponding sulfone (0.15 g, 31% yield). MS found: 482 (M+1).

(27i) Following a procedure analogous to that used in reaction (1l), the material from reaction (27h) (100 mg, 0.21 mmol) was converted to the corresponding hydroxamic acid (100 mg, 80% yield). MS found: 483 (M+1).

Example 28

N-hydroxy-2-{1-[({4-[(2-methyl-4-quinolinyl)methoxy]phenyl}sulfanyl)methyl]cyclohexyl}acetamide trifluoroacetate (28a) Following a procedure analogous to that used in reaction (1l), the material from reaction (27g) (160 mg, 0.35 mmol) was converted to the corresponding hydroxamic acid (150 mg, 76% yield). MS found: 451 (M+1).

Example 29

N-hydroxy-2-{3-[({4-[(2-methyl-4-quinolinyl)methoxy]phenyl}sulfonyl)methyl]-3-oxetanyl}acetamide trifluoroacetate (29a) To a solution of dimethyl allylmalonate (21.8 g, 126 mmol) in 250 mL of anhydrous DMF at 0° C. were added NaH (4.5 g, 60%, 200 mmol) and BOMCl (29.7 g, 200 mmol) subsequently. The mixture was stirred overnight and TLC showed no starting material left. The solvent was thus removed under reduced pressure and the residue was taken into 750 mL of ethyl acetate. The solution was washed with brine (200 mL×2) and it was dried over $MgSO_4$. After concentration, the residue was purified by column chromatography to provide the desired product (31.0 g, 84%). MS found: 293 (M+1).

(29b) To a suspension of LAH (12.4 g, 326 mmol) in 800 mL of anhydrous THF at 0° C. was added a solution of the material from reaction (29a) (38.1 g, 130 mmol) in 100 mL of THF. The mixture was stirred at room temperature overnight. The solution was cooled down to −78° C. and then 150 mL of ethyl acetate was slowly added. The solution was carefully warmed to 0° C. and then 150 mL of MeOH was added. Finally, 130 mL of HCl (1.0M) was added. The gelatinous material was filtered through a pad of Celite® and rinsed with ethyl acetate. After evaporation of the solvent under reduced pressure, the residue was purified by column chromatography to provide the desired product (18.3 g, 60% yield). MS found: 237 (M+1).

(29c) To a solution of the material from reaction (29b) (5.0 g, 21 mmol) in 75 mL of $C_2Cl_2$ at 0° C. were added DIEA (5.4 g, 42 mmol), catalytic DMAP (0.5 g) and TsCl (4.4 g, 23 mmol). The mixture was stirred for 2 days before it was worked up. The solution was diluted with ethyl acetate and the organic phase was washed with $H_2O$ (25 ml×2), brine (50 mL) and dried over $MgSO_4$. After filtration and concentration, the residue was purified by column chromatography to provide the desired product (4.0 g, 49% yield). MS found: 392 (M+1).

(29d) To a solution of the material from reaction (29c) (1.0 g, 2.6 mmol) in 100 mL of THF at −78° C. was added NaH (130 mg, 60%, 3.3 mmol). The solution was warmed to room temperature and was stirred overnight. After aqueous work-up and concentration, the residue was purified by column chromatography to provide the desired product (680 mg, >95% yield). MS found: 219 (M+1).

(29e) Following a procedure analogous to that used in reaction (1h), the material from reaction (29d) (1.2 g, 5.5 mmol) was converted to the aldehyde (640 mg, 53% yield). MS found: 441 (2M+1).

(29f) Following a procedure analogous to that used in reaction (1i), the aldehyde from reaction (29e) (640 mg, 2.9 mmol) was converted to the corresponding carboxylic acid (650 mg, >95% yield). MS found: 237 (M+1).

(29g) Following a procedure analogous to that used in reaction (1j), the acid from reaction (29f) (650 mg, 2.9 mmol) was converted to the methyl ester (670 mg, 90% yield). MS found: 250 (M+1).

(29h) To a solution of the material from reaction (29g) (670 mg, 2.7 mmol) in 20 mL of MeOH at room temperature was added Pd/C(100 mg). The solution was stirred under $H_2$ atmosphere overnight before the catalyst was filtered off. The solvent was removed under reduced pressure and the product (400 mg, 93% yield) was obtained without further purification. MS found: 161 (M+1).

(29i) Following a procedure analogous to that used in reaction (1d), the material from reaction (29h) (400 g, 2.5 mol) was converted to the mesylate (510 mg, >95% yield). MS found: 206 (M+1).

(29j) Following a procedure analogous to that used in reaction (1e), the mesylate from reaction (29i) (510 mg, 2.5 mmol) was converted to the corresponding sulfide (350 mg, 52% yield). MS found: 269 (M+1).

(29k) Following a procedure analogous to that used in reaction (1f) the material from reaction (29j) (350 mg, 1.3 mmol) was converted to the alkylation product (280 mg, 51% yield). MS found: 424 (M+1).

(29l) Following a procedure analogous to that used in reaction (1g), the material from reaction (29k) (280 mg, 0.68 mmol) was converted to the corresponding sulfone (250 mg, 80% yield). MS found: 456 (M+1).

(29m) Following a procedure analogous to that used in reaction (1l), the sulfone from reaction (29l) (50 mg, 0.11 mmol) was converted to the corresponding hydroxamic acid (45 mg, 72% yield). MS found: 457 (M+1).

Example 30

N-hydroxy-2-{1-methyl-3-[({4-[(2-methyl-4-quinolinyl)methoxy]phenyl}sulfonyl)methyl]-2-oxopyrrolidinyl}acetamide trifluoroacetate (30a) To a solution of diisopropylamine (15.4 mL, 110 mmol) in THF (200 mL) at −78° C. was added 2.5 M n-BuLi (44 mL, 110 mmol). The mixture was stirred at 0° C. for 30 min and cooled back to −78° C. To it was added a solution of 1-methyl-2-pyrrolidinone (9.9 g, 100 mmol) in THF (50 mL). After stirring at −78° C. for 1 h, a solution of allyl bromide (10.38 mL, 120 mmol) in THF (50 mL) was added. The mixture was allowed to stir at −30° C. for 2 h and the reaction was quenched with aqueous citric acid solution. EtOAc (300 mL) was added. The organic phase was separated, washed with brine 3×, dried ($MgSO_4$) and concentrated. Column chromatography eluting with EtOAc/hexanes (1:2) provided the allylated product (11.2 g, 73%). $MS(M+H)^+=140.1$.

(30b) To a freshly prepared solution of LDA (88 mmol) in THF (150 mL) at −78° C. was added a solution of compound 30a (11.2 g, 80.7 mmol) in THF (50 mL). After stirring at −78° C. for 1 h, a suspension of paraformaldehyde (10.6 g, 355 mmol) in THF (50 mL) was added. The mixture was allowed to stir at −30° C. for 4 h and the reaction was quenched with aqueous citric acid solution. EtOAc (200 mL) was added. The organic phase was separated, washed with brine 3×, dried ($MgSO_4$) and concentrated. Flash chromatography eluting with EtOAc/hexane (2:1) provided the desired alcohol (11.9 g, 87%). $MS(M+H)^+=170.1$.

(30c) To a solution of compound 30b (11.9 g, 70.3 mmol) in $C_2Cl_2$ cooled in an ice bath was added triethylamine (19.5 mL, 140 mmol) followed by methanesulfonyl chloride (7.7 mL, 100 mmol). The mixture was stirred at room temperature for 2 hours and the solvent was removed under reduced pressure. The residue was taken up in EtOAc (200 mL). The solution was washed with brine 2×, dried ($MgSO_4$) and concentrated. Column chromatography eluting with EtOAc/hexanes (2:1) provided the desired mesylate (10.9 g, 63%). $MS(M+H)^+=248.3$.

(30d) To a solution of 4-mercatophenol (7.57 g, 60 mmol) in DMF (40 mL) cooled in an ice bath was added NaH (4.0 g, 60% dispersion in mineral oil, 100 mmol). After stirring for 10 min, a solution of compound 30c (10.9 g, 40.4 mmol) in DMF (5 mL) was added to it. The mixture was allowed to stir at room temperature for 4 hours. EtOAc (300 mL) was added. The solution was washed with citric acid 2×, brine 3×, dried ($MgSO_4$) and concentrated. Column chromatography eluting with EtOAc/hexanes (1:1) afforded the desired sulfide (9.3 g, 82%). $MS(M+H)^+=278.3$.

(30e) A mixture of compound 30d (9.3 g, 33.5 mmol), 4-chloromethyl-2-methylquinoline hydrochloride (7.65 g, 33.5 mmol) and potassium carbonate (6.9 g, 50 mmol) in DMF (40 mL) was stirred at 80° C. for 2 hours. EtOAc (300 mL) was added. The solution was washed with brine 3×, dried ($MgSO_4$) and concentrated. Column chromatography eluting with EtOAc/hexanes (1:1) furnished the desired product (12.84 g, 88.5%). $MS(M+H)^+=433.2$.

(30f) To a solution of compound 30e (12.84 g, 29.68 mmol) in THF (90 mL) and MeOH (60 mL) was added a solution of Oxone® (36.8 g, 60 mmol) in water (120 mL). The solution was stirred at room temperature for 2 hours and concentrated to a small volume. EtOAc (200 mL) was added. The organic phase was separated, washed with brine 3×, dried ($MgSO_4$) and concentrated to give the sulfone product (11.8 g, 85%) that was pure enough for the next reaction. $MS(M+H)^+=465.1$.

(30g) Into a solution of compound 30f (11.8 g, 25.4 mmol) in $C_2Cl_2$ (500 mL) at −78° C. was bubbled oxygen for 10 min followed by ozone. After the solution turned blue, bubbling was continued for 15 more min. The flask was then flushed with nitrogen until the solution turned clear. Trimethylphosphite (6 mL, 50 mmol) was added. The solution was stirred at room temperature overnight and concentrated. Purification on a silica gel column eluting with 5% MeOH in $CH_2Cl_2$ provided the aldehyde (7.16 g, 60%). MS(M+ H)$^+$=467.2.

(30h) To a solution of compound 30g (7.16 g, 15.35 mmol) in 2-methyl-2-butene (33 mL) and 2-methyl-1-propanol (50 mL) was added a solution of sodium chlorite (10.4 g, 92 mmol) and sodium dihydrogenphosphate (5.53 g, 46 mmol) in water (34 mL). The mixture was stirred at room temperature for 2 h and acidified with 1 N HCl (pH=5). EtOAc (200 mL) was added. The organic phase was separated, washed with brine 3x, dried ($MgSO_4$) and concentrated. Column chromatography eluting with 10% MeOH in $CH_2Cl_2$ afforded the desired carboxylic acid (2.66 g, 36%). MS(M+H)$^+$=483.2.

(31i) A mixture of compound 30h (2.66 g, 5.51 mmol), iodomethane (1.6 mL, 25 mmol) and potassium carbonate (2.07 g, 15 mmol) in DMF (10 mL) was stirred at room temperature for 2 h. EtOAc (100 mL) was added. The solution was washed with brine 3x, dried ($MgSO_4$) and concentrated. Column chromatography eluting with EtOAc/hexanes (1:1) provided the methyl ester (1.98 g, 72%). MS(M+H)$^+$=497.2.

(30j) Compound 30i (200 mg, 0.40 mmol) was dissolved in 1.7 M $HONH_2$ solution (3 mL). After stirring at room temperature for 1 h, the solution was concentrated. Purification by reversed phase HPLC provided the hydroxamic acid (152 mg, 62%) as a powder. MS(M+H)$^+$=498.3.

Example 31

N-hydroxy-2-{1-[({4-[(2-methyl-4-quinolinyl)methoxy]phenyl}sulfonyl)methyl]cyclopentyl}acetamide trifluoroacetate (31a) To a freshly prepared LDA solution (~1.0 M, 46.8 mmol) at −78° C. was added a solution of methyl cyclopentanecarboxylate (5.0 g, 68 mmol) in 100 mL of anhydrous THF. The mixture stirred at −78° C. for 1 h and then a solution of allyl bromide (4.4 mL, 50.7 mmol) in 10 mL of anhydrous THF was added to it. The reaction mixture was gradually warmed up to 0° C. over 1.5 h. TLC revealed no more starting material left and the solvent was directly removed under reduced pressure. The residue was digested in 20% ether in hexane and the solution was filtered over a short pad of silica gel. The pad was washed with 20% of ether in hexane. After removal of the solvent of the combined organic layer, the desired product (6.0 g, 92% yield) was obtained and it was pure enough for next reaction based on $^1$H NMR evidence.

(31b) To a solution of the allylated compound (31a) (6.0 g, 35.7 mmol) in 400 mL of $CH_2Cl_2$ at −78° C. was added a solution of DIBAL in hexane (1.0 M, 107 mmol, 107 mL). The mixture was stirred at −78° C. for 2 h and TLC detected no starting material in solution. The excess DIBAL was quenched with 16.0 mL of MeOH, followed by the addition of 16.0 mL of $H_2O$. The suspension was kept stirring for 15 min before large excess amount of $Na_2SO_4$ was added. After the addition of $Na_2SO_4$, the supernatant was stirred for 1 h before it was filtered over celite. The pad of white solid was washed several times with ether. The solvent of the filtrate was removed under reduced pressure and the desired alcohol (4.7 g, 94% yield) was obtained. This material is pure enough for next reaction. MS found: 182 (M+1+$CH_3CN$).

(31c) To a solution of the material from reaction (31b) (4.7 g, 53.5 mmol) in 250 mL of $CH_2Cl_2$ was bubbled a flow of ozone until it turned to a blue solution. Trimethyl phosphite (8.3 g, 67 mmol) was added to it to reduce the ozonide overnight. After regular aqueous work-up and concentration, the residue was purified by column chromatography to provide the corresponding hemiacetal (1.8 g, 38% yield).

(31d) To a suspension of PDC(14.5 g, 39 mmol) in 150 mL of $C_2Cl_2$ were added 4A MS and the material from reaction (31c) (1.8 g, 12.9 mmol). The mixture was stirred overnight until TLC showed disappearance of the starting material. The mixture was filtered through a short pad of silica gel and rinsed with ether. The solvent was removed under reduced pressure. The product was obtained without further purification (1.3 g, 71.5% yield). MS found: 158 (M+$H_2O$).

(31e) To a suspension of NaH (0.66 g, 60%, 27.6 mmol) in 30 mL of DMF were added 4-mercaptophenol (2.32 g, 18.4 mmol) and the lactone from reaction (31d) (1.3 g, 9.2 mmol). The mixture was heated to 140° C. overnight and the solvent was removed under reduced pressure. The residue was dissolved in water and the aqueous solution was extracted with ethyl acetate (30 mLx2). The organic layer was set aside. The aqueous solution was acidified to pH=2.0 using HCl (1.0M) and the aqueous solution was extracted with ethyl acetate (50 mLx3). The combined organic phase was dried over $MgSO_4$ and the product (1.8 g, 74% yield) was obtained after evaporation of the solvent. MS found: 267 (M+1).

(31f) To a solution of the carboxylic acid (31e) (1.8 g, 6.7 mmol) in 100 mL of MeOH was added a solution of $TMSCHN_2$ (2.0 M in hexane) until the solution turned to yellow. The excess reagent was quenched with 2 drops of acetic acid and the solution was concentrated under reduced pressure. The residue (0.75 g, quantitative yield) thus obtained was pure enough for next reaction. MS found: 281 (M+1).

(31g) To a solution of the material (31f) (0.5 g, 1.8 mmol) in 7 mL of anhydrous DMF at room temperature were added tetrabutylammonium iodide (TBAI) (0.06 g, 0.1 eq.), $Cs_2CO_3$ (1.7 g, 5.4 mmol, 3 eq.), and 4-chloromethyl-2-methylquinoline hydrochloric acid (0.45 g, 2.0 mmol). The mixture stirred at 80° C. for 12 h. TLC revealed no starting material left and the suspension was diluted with ether. The etherate was filtered over a short pad of silica gel and the pad was washed with ether several times. The combined filtrate was evaporated under vacuum and the residue was purified on column chromatography using 35% ethyl acetate in hexane. The desired product was isolated (0.41 g, 53% yield). MS found: 436 (M+1).

(31h) Oxone® (1.15 g, 1.9 mmol) was dissolved in 20 mL of $H_2O$. In another flask, the product from reaction (31g) (0.41 g, 0.94 mmol) was dissolved in a mixture of 40 mL of MeOH. The Oxone® solution was added to it and the mixture was allowed to stir for 2 h. The pH of the solution was adjusted to 10 using $Na_2CO_3$ and the aqueous solution was extracted with ethyl acetate (50 mLx2). The combined organic phase was washed with brine and dries over $MgSO_4$. After evaporation of the solvent, the sulfone product was obtained (0.41 g, 93% yield). MS found: 468 (M+1).

(31i) To a flask containing the material (75 mg, 0.16 mmol) obtained from (31h) was added a solution of $NH_2OH/NaOMe/MeOH$ (1.64 M, 2.0 mL) at room temperature. The mixture stirred for 60 min and then was quenched with TFA to pH=7. After evaporation of MeOH, the residue was purified on HPLC and the final hydroxamic acid was obtained (50 mg, 54% yield). MS found: 469 (M+1).

Example 32

N-hydroxy-2-[5-[({4-[(2-methyl-4-quinolinyl)methoxy]phenyl}sulfonyl)methyl]-3-(3-pyridinyl)-4,5-dihydro-5-isoxazolyl]acetamide bis (trifluoroacetate)

(32a) To a solution of itaconic acid mono-n-butyl ester (9.31 g, 50 mmol) and triethylamine (6.96 mL, 50 mmol) in THF (100 mL) cooled in an ice bath was added n-propyl chloroformate (5.58 mL, 50 mmol). After stirring for 30 min, the salt formed was filtered off. The filtrate was cooled in an ice bath. Sodium borohydride (3.59 g, 95 mmol) was added in batches over a period of 30 min. After stirring at 0–10° C. for 5 hours, the reaction was quenched with 1 N HCl. Ethyl ether was added. The organic layer was washed with brine 3×, dried (MgSO$_4$) and concentrated. Flash chromatography eluting with EtOAc/hexanes (1:1) provided the desired alcohol (2.5 g, 29%). MS (M+H)$^+$=173.1.

(32b) To a solution of compound 32a (250 mg, 1.45 mmol) and 3-pyridinealdoxime (177 mg, 1.45 mmol) in C$_2$Cl$_2$ (5 mL) was added a solution of bleach (3 mL). The mixture was stirred at room temperature for 2 hours. The solution was diluted with CH$_2$Cl$_2$. The organic phase was separated, washed with brine 2×, dried (MgSO$_4$) and concentrated. Column chromatography eluting with 60% EtOAc in hexanes provided the isoxazoline derivative (150 mg, 35%). MS(M+H)$^+$=293.1.

(32c) To a solution of compound 32b (150 mg, 0.51 mmol) in CHCl$_3$ (3 mL) cooled in an ice bath was added triethylamine (202 mg, 2 mmol) followed by methanesulfonyl chloride (114 mg, 1 mmol). After stirring for 1 h, the solvent was removed under reduced pressure. The residue was taken up in EtOAc. The solution was washed with brine 3×, dried (MgSO$_4$) and concentrated to give the desired mesylate. MS (M+H)$^+$=371.2.

(32d) To a solution of 4-mercatophenol (126 mg, 1 mmol) in DMF (2 mL) cooled in an ice bath was added NaH (80 mg, 60% dispersion in mineral oil, 2 mmol). After stirring under nitrogen for 5 min, a solution of compound 32c (185 mg, 0.5 mmol) in DMF (2 mL) was added. The mixture was stirred at room temperature overnight. EtOAc was added. The solution was washed with 1 N HCl 1×, brine 2×, dried (MgSO$_4$) and concentrated. Flash chromatography eluting with EtOAc/hexanes (2:1) provided the sulfide product (70 mg, 35%). MS(M+Na)$^+$=423.

(32e) Following the procedure described in (31e), compound 32d was subjected to an alkylation with 4-chloromethyl-2-methylquinoline. MS(M+H)$^+$=556.3.

(32f) Following the procedure described in (31f), compound 32e was oxidized using Oxone® to furnish the sulfone derivative. MS(M+H)$^+$=588.3.

(32g) Following the procedure described in (31j), compound 32f was converted to a hydroxamic acid. MS(M+H)$^+$=546.3.

Example 33

N-Hydroxy-2-[5-[({4-[(2-methyl-4-quinolinyl)methoxy]phenyl}sulfonyl)methyl]-3-(4-pyridinyl)-4,5-dihydro-5-isoxazolyl]acetamide bis (trifluoroacetate)

This compound was prepared using procedures analogous to those described for Example 32. MS(M+H)$^+$=546.3.

Example 34

N-hydroxy-2-{4-[({4-[(2-methyl-4-quinolinyl)methoxy]phenyl}sulfonyl)methyl]tetrahydro-2H-pyran-4-yl}acetamide trifluoroacetate (34a) Following a procedure analogous to that used in reaction (1a), tetrahydro-pyran-4-carboxylic acid (2.36 g, 18 mmol) was converted to its methyl ester (2.53 g, 97% yield). MS found: 145 (M+1).

(34b) Following a procedure analogous to that used in reaction (1b), the methyl ester from (34a) (1.16 g, 8 mmol) was transformed to the allylation product (1.45 g, >95% yield). MS found: 185 (M+1).

(34c) Following a procedure analogous to that used in reaction (1c), the material from reaction (34b) (1.93 g, 10 mmol) was reduced to the corresponding alcohol (1.13 g, 70% yield). MS found: 157 (M+1).

(34d) Following a procedure analogous to that used in reaction (25c), the material from reaction (34c) (1.13 g, 7.2 mmol) was converted to the corresponding hemiacetal (0.12 g, 10% yield).

(34e) Following a procedure analogous to that used in reaction (25d), the material from reaction (34d) (0.12 g, 0.77 mmol) was oxidized to the corresponding lactone (0.08 g, 66% yield).

(34f) Following a procedure analogous to that used in reaction (25e), the material from reaction (34e) (80 mg, 0.51 mmol) was converted to the corresponding sulfide (80 mg, 56% yield).

(34g) Following a procedure analogous to that used in reaction (1j), the material from reaction (34f) (80 mg, 0.3 mmol) was converted to the corresponding methyl ester (93 mg, >95% yield). MS found: 297 (M+1).

(34h) Following a procedure analogous to that used in reaction (1f), the material from reaction (34g) (90 mg, 0.3 mmol) was converted to the corresponding alkylation product (37 mg, 27% yield). MS found: 452 (M+1).

(34i) Following a procedure analogous to that used in reaction (1g), the material from reaction (34h) (37 mg, 0.08 mmol) was converted to the corresponding sulfone (36 mg, >95% yield).

(34j) Following a procedure analogous to that used in reaction (11), the material from reaction (34i) (36 mg, 0.07 mmol) was converted to the corresponding hydroxamic acid (10 mg, 30% yield). MS found: 485 (M+1).

TABLE 1

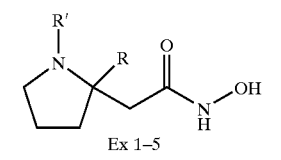

Ex 1–5

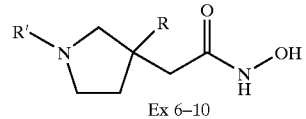

Ex 6–10

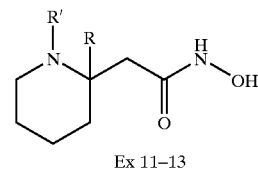

Ex 11–13

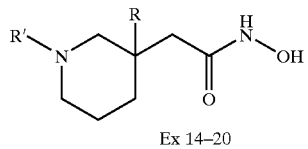

Ex 14–20

TABLE 1-continued

Ex 21–22: piperidine with R at 4-position, N-R', CH2C(O)NHOH

Ex 23: tetrahydrofuran with R, CH2C(O)NHOH

Ex 24–26: cyclobutane with R, CH2C(O)NHOH

Ex 27–28: cyclohexane with R, CH2C(O)NHOH

Ex 29: oxetane with R, CH2C(O)NHOH

Ex 30: 2-oxopyrrolidine N-R', with R, CH2C(O)NHOH

Ex 31: cyclopentane with R, CH2C(O)NHOH

Ex 32–33: isoxazoline with R', R, CH2C(O)NHOH

Ex 34: tetrahydropyran with R, CH2C(O)NHOH

| Ex # | R | R' | MS [M + 1] |
|---|---|---|---|
| 1 | 4-[({2-methyl-4-quinolinyl}methoxy)phenyl-sulfonyl]methyl | H | 470 |
| 2 | 4-[({2-methyl-4-quinolinyl}methoxy)phenyl-sulfonyl]methyl | methyl | 484 |
| 3 | 4-[({2-methyl-4-quinolinyl}methoxy)phenyl-sulfonyl]methyl | isobutyl | 526 |
| 4 | 4-[({2-methyl-4-quinolinyl}methoxy)phenyl-sulfonyl]methyl | 3-pyridinyl | 561 |
| 5 | 4-[({2-methyl-4-quinolinyl}methoxy)phenyl-sulfonyl]methyl | acetyl | 512 |
| 6 | 4-[({2-methyl-4-quinolinyl}methoxy)phenyl-sulfonyl]methyl | H | 470 |
| 7 | 4-[({2-methyl-4-quinolinyl}methoxy)phenyl-sulfonyl]methyl | methyl | 484 |
| 8 | 4-[({2-methyl-4-quinolinyl}methoxy)phenyl-sulfonyl]methyl | isopropyl | 512 |
| 9 | 4-[({2-methyl-4-quinolinyl}methoxy)phenyl-sulfonyl]methyl | isobutyl | 526 |
| 10 | 4-[({2-methyl-4-quinolinyl}methoxy)phenyl-sulfonyl]methyl | neopentyl | 540 |
| 11 | 4-[({2-methyl-4-quinolinyl}methoxy)phenyl-sulfonyl]methyl | H | 484 |
| 12 | 4-[({2-methyl-4-quinolinyl}methoxy)phenyl-sulfonyl]methyl | methyl | 498 |
| 13 | 4-[({2-methyl-4-quinolinyl}methoxy)phenyl-sulfonyl]methyl | isobutyl | 540 |
| 14 | 4-[({2-methyl-4-quinolinyl}methoxy)phenyl-sulfinyl]methyl | H | 468 |
| 15 | 4-[({2-methyl-4-quinolinyl}methoxy)phenyl-sulfinyl]methyl | methyl | 482 |
| 16 | 4-[({2-methyl-4-quinolinyl}methoxy)phenyl-sulfinyl]methyl | isopropyl | 510 |
| 17 | 4-[({2-methyl-4-quinolinyl}methoxy)phenyl-sulfonyl]methyl | H | 484 |
| 18 | 4-[({2-methyl-4-quinolinyl}methoxy)phenyl-sulfonyl]methyl | methyl | 498 |
| 19 | 4-[({2-methyl-4-quinolinyl}methoxy)phenyl-sulfonyl]methyl | isopropyl | 526 |
| 20 | 4-[({2-methyl-4-quinolinyl}methoxy)phenyl-sulfonyl]methyl | isobutyl | 540 |
| 21 | 4-[({2-methyl-4-quinolinyl}methoxy)phenyl-sulfonyl]methyl | H | 484 |
| 22 | 4-[({2-methyl-4-quinolinyl}methoxy)phenyl-sulfonyl]methyl | methyl | 498 |
| 23 | 4-[({2-methyl-4-quinolinyl}methoxy)phenyl-sulfonyl]methyl | — | 471 |
| 24 | 4-[({2-methyl-4-quinolinyl}methoxy)phenyl-sulfonyl]methyl | — | 455 |
| 25 | 4-[({2-methyl-4-quinolinyl}methoxy)phenyl-sulfinyl]methyl | — | 439 |
| 26 | 4-[({2-methyl-4-quinolinyl}methoxy)phenyl-sulfanyl]methyl | — | 423 |
| 27 | 4-[({2-methyl-4-quinolinyl}methoxy)phenyl-sulfonyl]methyl | — | 483 |
| 28 | 4-[({2-methyl-4-quinolinyl}methoxy)phenyl-sulfonyl]methyl | — | 451 |
| 29 | 4-[({2-methyl-4-quinolinyl}methoxy)phenyl-sulfonyl]methyl | — | 457 |
| 30 | 4-[({2-methyl-4-quinolinyl}methoxy)phenyl-sulfonyl]methyl | methyl | 498 |
| 31 | 4-[({2-methyl-4-quinolinyl}methoxy)phenyl-sulfonyl]methyl | — | 469 |
| 32 | 4-[({2-methyl-4-quinolinyl}methoxy)phenyl-sulfonyl]methyl | 3-pyridinyl | 546 |
| 33 | 4-[({2-methyl-4-quinolinyl}methoxy)phenyl-sulfonyl]methyl | 4-pyridinyl | 546 |
| 34 | 4-[({2-methyl-4-quinolinyl}methoxy)phenyl-sulfonyl]methyl | — | 485 |

The following tables contain representative examples of the present invention. Each entry in each table is intended to be paired with each formula at the start of the table. For example, example 1 is intended to be paired with each of formulae A–Z.

TABLE 2
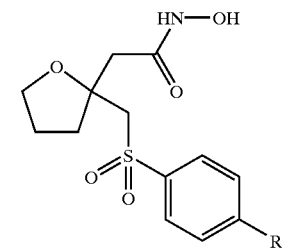 A
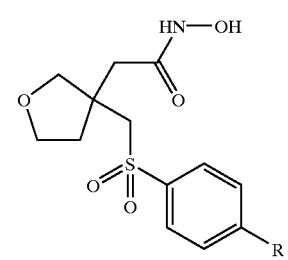 B
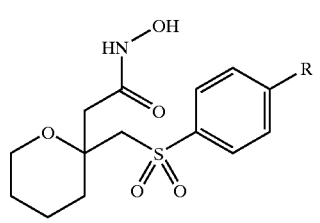 C
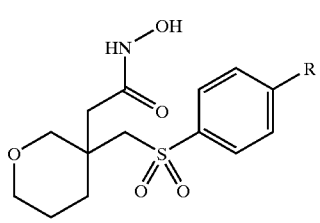 D
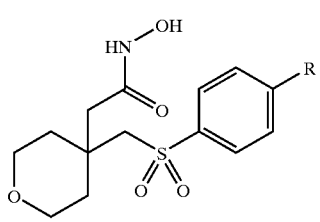 E
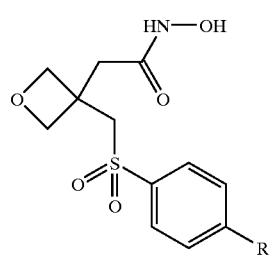 F
TABLE 2-continued
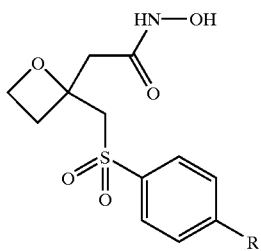 G
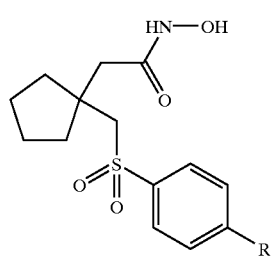 H
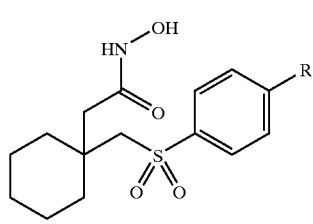 I
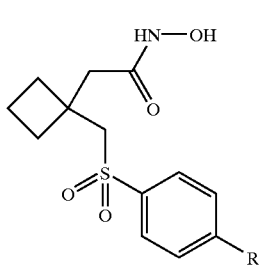 J
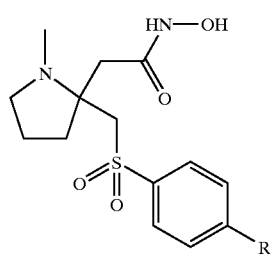 K
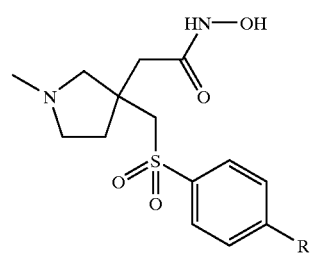 L TABLE 2-continued

M

N

O

P

| Entry # | R |
|---|---|
| 1 | (2-methyl-4-quinolinyl)methoxy |
| 2 | (2-methyl-4-quinolinyl)methylamino |
| 3 | N-methyl-(2-methyl-4-quinolinyl)methylamino |
| 4 | 1-hydroxy-2-(2-methyl-4-quinolinyl)ethyl |
| 5 | 1-methoxy-2-(2-methyl-4-quinolinyl)ethyl |
| 6 | 1-hydroxy-1-methyl-2-(2-methyl-4-quinolinyl)ethyl |
| 7 | 1-amino-2-(2-methyl-4-quinolinyl)ethyl |
| 8 | 1-(methylamino)-2-(2-methyl-4-quinolinyl)ethyl |
| 9 | 1-(dimethylamino)-2-(2-methyl-4-quinolinyl)ethyl |
| 10 | [(2-methyl-4-quinolinyl)oxy]methyl |
| 11 | [(2-methyl-4-quinolinyl)amino]methyl |
| 12 | [methyl(2-methyl-4-quinolinyl)amino]methyl |
| 13 | (2-methyl-4-quinolinyl)oxy |
| 14 | (2-methyl-4-quinolinyl)amino |
| 15 | [methyl(2-methyl-4-quinolinyl)]amino |
| 16 | [hydroxy(2-methyl-4-quinolinyl)]methyl |
| 17 | [1-hydroxy-1-(2-methyl-4-quinolinyl)]ethyl |
| 18 | 1-methoxy-1-(2-methyl-4-quinolinyl)]ethyl |
| 19 | methoxy(2-methyl-4-quinolinyl)]methyl |
| 20 | amino(2-methyl-4-quinolinyl)methyl |
| 21 | (methylamino)(2-methyl-4-quinolinyl)methyl |
| 22 | (dimethylamino)(2-methyl-4-quinolinyl)methyl |

TABLE 3

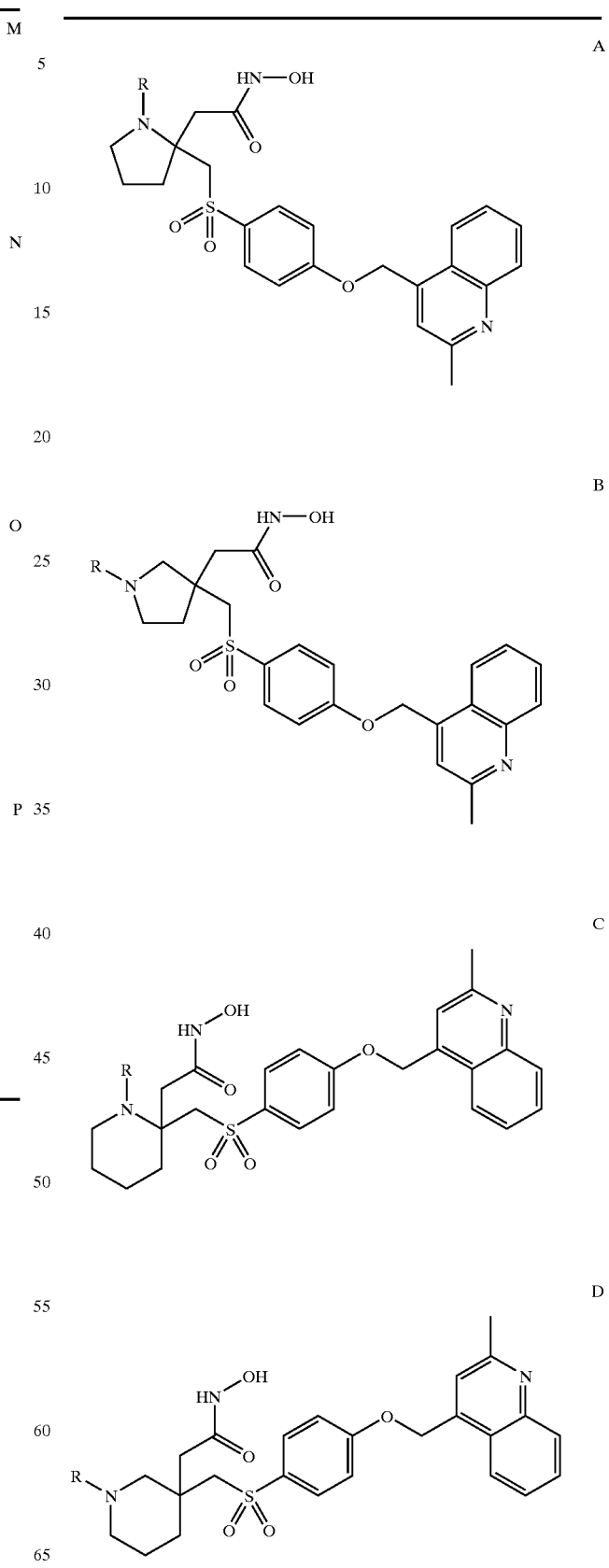

TABLE 3-continued

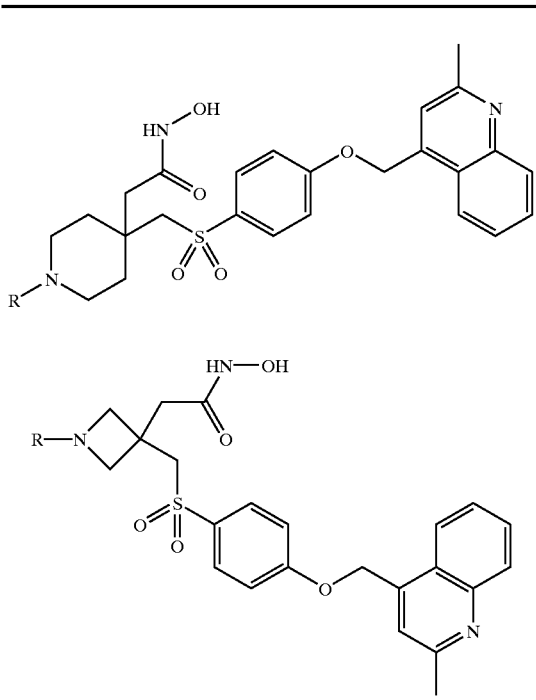

| Entry # | R |
|---|---|
| 1 | H |
| 2 | methyl |
| 3 | ethyl |
| 4 | 1-methylethyl |
| 5 | cyclobutyl |
| 6 | n-butyl |
| 7 | 2,2-dimethylpropyl |
| 8 | cyclopropylmethyl |
| 9 | 2-methoxyethyl |
| 10 | 2-hydroxyethyl |
| 11 | aminoethyl |
| 12 | 2-dimethylaminoethyl |
| 13 | 2-(4-morpholinyl)ethyl |
| 14 | 2-(1-piperidinyl)ethyl |
| 15 | 2-(1-piperizinyl)ethyl |
| 16 | phenyl |
| 17 | benzyl |
| 18 | 3-picolyl |
| 19 | formyl |
| 20 | acetyl |
| 21 | pivaloyl |
| 22 | benzoyl |
| 23 | nicotinoyl |
| 24 | methanesulfonyl |
| 25 | benzenesulfonyl |
| 26 | t-butylsulfonyl |
| 27 | methoxycarbonyl |
| 28 | t-butyoxycarbonyl |
| 29 | isopropyloxycarbonyl |
| 30 | dimethylcarbamyl |
| 31 | 4-morpholinecarbonyl |
| 32 | 2-thiophenecarbonyl |
| 33 | 2-fluoroethyl |
| 34 | 2,2-difluoroethyl |
| 35 | 2-(dimethylamino)-2-oxoethyl |
| 36 | 2-oxo-2-(4-morpholinyl)ethyl |
| 37 | t-butyl |
| 38 | 1,1-dimethylpropyl |
| 39 | 2-propenyl |
| 40 | 1-methyl-2-propenyl |
| 41 | 1,1-dimethyl-2-propenyl |
| 42 | 2-propynyl |
| 43 | 1-methyl-2-propynyl |
| 44 | 1,1-dimethyl-2-propynyl |
| 45 | (2-pyrrolidinyl)methyl |

Utility

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TNF and/or Aggrecanase and/or MP's are potentially useful for the treatment or prophylaxis of various inflammatory, infectious, immunological or malignant diseases. These include, but are not limited to Cachexia includes cachexia resulting from cancer, HIV, congestive heart failure (CHF), and any chronic disease. Rheumatoid arthritis includes early, juvenile (including juvenile chronic arthritis), and adult rheumatoid arthritis. Shock includes septic and haemodynamic shock. Spondylitis includes ankylosing spondiylitis. Cachexia includes cachexia resulting from cancer, HIV, congestive heart failure (CHF), and any chronic disease. Rheumatoid arthritis includes early, juvenile (including juvenile chronic arthritis), and adult rheumatoid arthritis. Shock includes septic and haemodynamic shock. Spondylitis includes ankylosing spondiylitis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$'s or $IC_{50}$'s of $\leq 1$ µM. More preferred compounds of the present invention have $K_i$'s or $IC_{50}$'s of $\leq 0.1$ µM. Even more preferred compounds of the present invention have $K_i$'s or $IC_{50}$'s of $\leq 0.01$ µM. Still more preferred compounds of the present invention have $K_i$'s or $IC_{50}$'s of $\leq 0.001$ µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. *Trans. Ortho. Res. Soc.* 1995, 20, 341). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteases released into the media during aggrecanase accumulation, agents that inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 µM for aggrecanase.

To evaluate inhibition of aggrecanase, compounds are prepared as 10 mM stocks in DMSO, water or other solvents and diluted to appropriate concentrations in water. Drug (50 uL) is added to 50 uL of aggrecanase-containing media and 50 uL of 2 mg/ml aggrecan substrate and brought to a final volume of 200 uL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC(0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2 \times 10^6$ cells/ml in 96 well polystyrene plates. Cells were preincubated 10 minutes with compound, then stimulated with 1 µg/ml LPS(Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 uL of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Counterscreens

The enzymatic activities of recombinant MMP-1, 2, 3, 9, and 13 were measured at 25° C. with a fluorometric assay (Copeland, R. A.; Lombardo, D.; Giannaras, J. and Decicco, C. P. *Bioorganic Med. Chem. Lett.* 1995, 5 , 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis,* Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq 10$ $\mu$M. Preferred compounds of the present invention have $K_i$'s of $\leq 1$ $\mu$M. More preferred compounds of the present invention have $K_i$'s of $\leq 0.1$ $\mu$M. Even more preferred compounds of the present invention have $K_i$'s of $\leq 0.01$ $\mu$M. Still more preferred compounds of the present invention have $K_i$'s of $\leq 0.001$ $\mu$M.

Using the methodology described above, a number of compounds of the present invention were found to exhibit $K_i$'s of $\leq 10$ $\mu$M, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration; the renal and hepatic function of the patient; and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of this invention from being realized.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:
1. A compound of formula I:

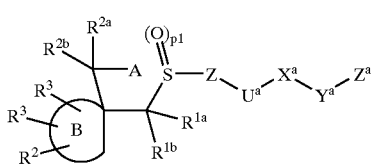

or a stereoisomer or pharmaceutically acceptable salt form thereof, wherein;

A is selected from $-COR^5$, $-CO_2H$, $CH_2CO_2H$, $-CO_2R^6$, $-CONHOH$, $-CONHOR^5$, $-CONHOR^6$, $-N(OH)CHO$, $-N(OH)COR^5$, $-SH$, $-CH_2SH$, $-SONHR^a$, $-SN_2H_2R^a$, $-PO(OH)_2$, and $-PO(OH)NHR^a$;

ring B is a 5–6 membered heterocyclic ring consisting of: carbon atoms, 0–1 carbonyl groups, 0–1 double bonds, and from 0–2 ring heteroatoms selected from O, N, $NR^2$, and $S(O)_p$, provided that ring B contains other than a S—S, O—O, or O—O, or S—O bond and provided that N—$R^2$ forms other than an N—O, N—N, or N—S bond;

Z is phenyl substituted with 0–4 $R^b$;
$U^a$ is O;
$X^a$ is absent or selected from $C_{1-10}$ alkylene, $C_{2-10}$ alkenylene, and $C_{2-10}$ alkynylene;
$Y^a$ is absent or selected from O, $NR^{a1}$, $S(O)_p$, and $C(O)$;
$Z^a$ isquinolinyl substituted with 0–5 $R^c$;
provided that Z, $U^a$, $Y^a$, and $Z^a$ do not combine to form a O—N, O—O, or O—$S(O)_p$ group;
$R^{1a}$ is selected from H, $C_{1-4}$ alkyl, phenyl, benzyl, $CH_2OR^3$, and $CH_2NR^aR^{a1}$;
$R^{1b}$ is selected from H, $C_{1-4}$ alkyl, phenyl, benzyl, $CH_2OR^3$, and $CH_2NR^aR^{a1}$;

alternatively, $R^{1a}$ and $R^{1b}$ combine to form a 3–6 membered ring consisting of: carbon atoms and 0–1 heteroatoms selected from O, S, S(O), $S(O)_2$, and $NR^a$;
provided that when $R^{1a}$ and $R^{1b}$ are hydrogen and ring B is a heterocycle, then $Z^a$ is the following:

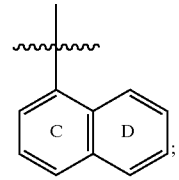

ring C is phenyl or pyridyl and is substituted with 0–2 $R^c$;
ring D is selected from phenyl, pyridyl, pyridazinyl, pyrimidyl, and pyrazinyl, and is substituted with 0–3 $R^c$;
$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_{r1}OC(O)(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q, $(CR^aR^{a1})_{r1}NR^aC(O)(CR^aR^{a1})_r$-Q, $(CR^aR^{a1})_{r1}OC(O)O(CR^aR^{a1})_r$-Q, $(CR^aR^{a1})_{r1}OC(O)NR^a(CR^aR^{a1})_r$-Q, $(CR^aR^{a1})_{r1}NR^aC(O)O(CR^aR^{a1})_r$-Q, $(CR^aR^{a1})_{r1}NR^aC(O)NR^a(CR^aR^{a1})_r$-Q, $(CR^aR^{a1})_{r1}S(O)_p(CR^aR^{a1})_r$-Q, $(CR^aR^{a1})_{r1}SO_2NR^a(CR^aR^{a1})_r$-Q, $(CR^aR^{a1})_{r1}NR^aSO_2(CR^aR^{a1})_r$-Q, and $(CR^aR^{a1})_{r1}NR^aSO_2NR^a(CR^aR^{a1})_r$-Q;

$R^{2a}$ is selected from H, $C_{1-14}$ alkyl, phenyl, benzyl, $CH_2OR^3$, and $CH_2NR^aR^{a1}$;
$R^{2b}$ is selected from H, $C_{1-4}$ alkyl, phenyl, benzyl, $CH_2OR^3$, and $CH_2NR^aR^{a1}$;
alternatively, $R^{2a}$ and $R^{2b}$ combine to form a 3–6 membered ring consisting of: carbon atoms and 0–1 heteroatoms selected from O, S, S(O), $S(O)_2$, and $NR^a$;
Q is selected from H, a $C_{3-13}$ carbocyclic residue substituted with 0–5 $R^d$ and a 5–14 membered heterocycle consisting of: carbon atoms and 1–4 heteroatoms selected from the group consisting of N, O, and $S(O)_p$ and substituted with 0–5 $R^d$;
$R^3$, at each occurrence, is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1}_2)_{r1}S(O)_p(CR^aR^{a1})_r$-$Q^1$, and $(CR^aR^{a1})_{r1}SO_2NR^a(CR^aR^{a1})_r$-$Q^1$;
alternatively, when two $R^3$'s are attached to the same carbon atom, they combine to form a 3–8 membered carbocyclic or heterocyclic ring consisting of: carbon atoms and
0–3 heteroatoms selected from the group consisting of N, O, and $S(O)_p$ and substituted with 0–3 $R^d$;
$Q^1$ is selected from H, phenyl substituted with 0–3 $R^d$, naphthyl substituted with 0–3 $R^d$ and a 5–10 membered heteroaryl consisting of: carbon atoms and 1–4 heteroatoms selected from the group consisting of N, O, and S and substituted with 0–3 $R^d$;
$R^a$, at each occurrence, is independently selected from H, $C_{1-4}$ alkyl, phenyl and benzyl;
$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocyclic residue and a 5–14 membered heterocycle consisting of: carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocyclic residue and a 5–14 membered heterocycle consisting of: carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl —$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

p1 is selected from 0, 1, and 2;

r, at each occurrence, is selected from 0, 1, 2, 3, and 4; and, r1, at each occurrence, is selected from 0, 1, 2, 3, and 4.

2. A compound according to claim 1, wherein the compound is of formula II:

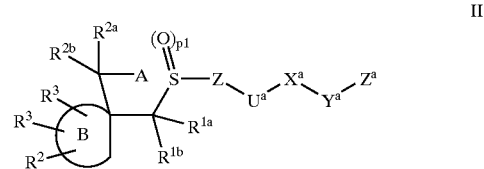

or a stereoisomer or pharmaceutically acceptable salt form thereof, wherein;

A is selected from —$CO_2H$, $CH_2CO_2H$, —CONHOH, —$CONHOR^5$, —$CONHOR^6$, —N(OH)CHO, —N(OH)$COR^5$, —SH, and —$CH_2SH$;

ring B is a 5–6 membered heterocyclic ring consisting of: carbon atoms, 0–1 carbonyl groups, 0–1 doublebonds, and from 0–2 ring heteroatoms selected from O, N, and $NR^2$, provided that ring B contains other than an O—O bond and provided that N—$R^2$ forms other than an N—O, N—N, or N—S bond;

$X^a$ is absent or selected from $C_{1-4}$ alkylene and $C_{2-4}$ alkynylene;

$Y^a$ is absent or selected from O and $NR^{a1}$;

provided that Z, $U^a$, $Y^a$, and $Z^a$ do not combine to form a O—N or O—O group;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)CR^aR^{a1})_r$-Q, $(CR^aR^{a1})_{r1}C(O)O(CR^aR^{a1})_r$-Q, $(CR^aR^{a1})_rC(O)NR^aR^{a1}$, $(CR^aR^{a1})_{r1}C(O)NR^a(CR^aR^{a1})_r$-Q, $(CR^aR^{a1})_{r1}S(O)p(CR^aR^{a1})_r$-Q, and $(CR^aR^{a1})_{r1}SO_2NR^a(CR^aR^{a1})_r$-Q;

Q is selected from H, a $C_{3-6}$ carbocyclic residue substituted with 0–5 $R^d$, and a 5–10 membered heterocycle consisting of: carbon atoms and 1–4 heteroatoms selected from the group consisting of N, O, and $S(O)_p$ and substituted with 0–5 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocyclic residue and a 5–6 membered heterocycle consisting of: carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, $C(O)$ $R^a$, $C(O)OR^a$, $C(O)NR^aR^{a1}$, $S(O)_2NR^aR^{a1}$, $S(O)_pR^{a2}$, $CF_3$, $C_{3-6}$ carbocyclic residue and a 5–6 membered heterocycle consisting of: carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

3. A compound according to claim 2, wherein the compound is of formula III:

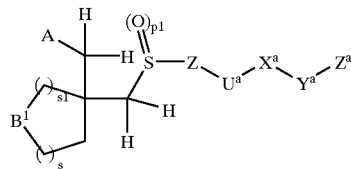

III or a stereoisomer or pharmaceutically acceptable salt form thereof, wherein;

A is selected from —$CO_2H$, $CH_2CO_2H$, —CONHOH, —$CONHOR^5$, —N(OH)CHO, and —$N(OH)COR^5$;

$B^1$ is $NR^2$ or O;

Z is phenyl substituted with 0–3 $R^b$;

$X^a$ is absent or selected from $C_{1-2}$ alkylene and $C_{2-4}$ alkynylene;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_r$-Q, $(CR^aR^{a1})_{r1}C(O)O(CR^aR^{a1})_r$-Q, $(CR^aR^{a2})_{r1}C(O)NR^aR^{a1}$, $(CR^aR^{a2})_{r1}C(O)NR^a(CR^aR^{a1})_r$-Q, and $(CR^aR^{a1})_{r1}S(O)_p(CR^aR^{a1})_r$-Q;

Q is selected from H, a $C_{3-6}$ carbocyclic residue substituted with 0–3 $R^d$ and a 5–10 membered heterocycle consisting of: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^{a1}R^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

r1, at each occurrence, is selected from 0, 1, 2, 3, and 4; and, s and s1 combine to total 1, 2, 3, or 4.

4. A compound according to claim 3, wherein the compound is of formula IV:

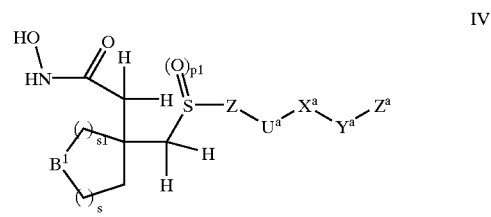

IV or a stereoisomer or pharmaceutically acceptable salt form thereof, wherein;

Z is phenyl substituted with 0–3 $R^b$;

$X^a$ is absent or is selected from $CR^2$, $CH_2CH_2$, and $C_{2-4}$ alkynylene;

$Y^a$ is absent or is O;

$Z^a$ is quinolinyl substituted with 0–3 $R^c$;

provided that Z, $U^a$, $Y^a$, and $Z^a$ do not combine to form a O—O group;

$R^2$ is selected from Q, $C_{1-6}$ alkylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, CH$_3$, and CH$_2$CH$_3$;

$R^{a1}$, at each occurrence, is independently selected from H, CH$_3$, and CH$_2$CH$_3$;

$R^{a2}$, at each occurrence, is independently selected from H, CH$_3$, and CH$_2$CH$_3$;

$R^b$, at each occurrence, is independently selected from C$_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, and CF$_3$;

$R^c$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, and CF$_3$;

$R^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$ and phenyl;

p, at each occurrence, is selected from 0, 1, and 2;

r, at each occurrence, is selected from 0, 1, 2, and 3;

r1, at each occurrence, is selected from 0, 1, 2, and 3; and, s and s1 combine to total 2, 3, or 4.

5. A compound according to claim 1, wherein the compound is selected from the group:

N-hydroxy-2-{2-[({4-[2-methyl-4-quinolinyl)methoxy]phenyl}sulfonyl)methyl]-2-pyrrolidinyl}acetamide;

N-hydroxy-2-{1-methyl-2-[({4-[(2-methyl-4-quinolinyl)methoxy]phenyl}sulfonyl)methyl]-2-pyrrolidinyl}acetamide;

N-hydroxy-2-{1-isobutyl-2-[({4-[(2-methyl-4-quinolinyl)methoxy]phenyl}sulfonyl)methyl]-2-pyrrolidinyl}acetamide;

N-hydroxy-2-{2-[({4-[(2-methyl-4-quinolinyl)methoxy]phenyl}sulfonyl)methyl]-1-(3-pyridinyl)-2-pyrrolidinyl}acetamide;

2-{1-acetyl-2-[({4-[(2-methyl-4-quinolinyl)methoxy]phenyl}sulfonyl)methyl]-2-pyrrolidinyl}-N-hydroxyacetamide;

N-hydroxy-2-{3-[({4-{(2-methyl-4-quinolinyl)methoxy]phenyl}sulfonyl)methyl]-3-pyrrolidinyl}acetamide;

N-hydroxy-2-{1-methyl-3-[({4-{(2-methyl-4-quinolinyl)methoxy]phenyl}sulfonyl)methyl]-3-pyrrolidinyl}acetamide;

N-hydroxy-2-{1-isopropyl-3-[({4-{(2-methyl-4-quinolinyl)methoxy]phenyl}sulfonyl)methyl]-3-pyrrolidinyl}acetamide;

N-hydroxy-2-{1-isobutyl-3-[({4-{(2-methyl-4-quinolinyl)methoxy]phenyl}sulfonyl)methyl]-3-pyrrolidinyl}acetamide;

N-hydroxy-2-{3-[({4-{(2-methyl-4-quinolinyl)methoxy]phenyl}sulfonyl)methyl]-1-neopentyl-3-pyrrolidinyl}acetamide;

N-hydroxy-2-{2-[({4-[(2-methyl-4-quinolinyl)methoxy]phenyl}sulfonyl)methyl]-2-piperidinyl}acetamide;

N-hydroxy-2-{1-methyl-2-[({4-[(2-methyl-4-quinolinyl)methoxy]phenyl}sulfonyl)methyl]-2-piperidinyl}acetamide;

N-hydroxy-2-{1-isobutyl-2-[({4-[(2-methyl-4-quinolinyl)methoxy]phenyl}sulfonyl)methyl]-2-piperidinyl}acetamide;

N-hydroxy-2-{3-[({4-[(2-methyl-4-quinolinyl)methoxy]phenyl}sulfinyl)methyl]-3-piperidinyl}acetamide;

N-hydroxy-2-{1-methyl-3-[({4-[(2-methyl-4-quinolinyl)methoxy]phenyl}sulfinyl)methyl]-3-piperidinyl}acetamide N-hydroxy-2-{1-isopropyl-3-[({4-[(2-methyl-4-quinolinyl)methoxy]phenyl}sulfinyl)methyl]-3-piperidinyl}acetamide;

N-hydroxy-2-{3-[({4-[(2-methyl-4-quinolinyl)methoxy]phenyl}sulfonyl)methyl]-3-piperidinyl}acetamide;

N-hydroxy-2-{1-methyl-3-[({4-[(2-methyl-4-quinolinyl)methoxy]phenyl}sulfonyl)methyl]-3-piperidinyl}acetamide;

N-hydroxy-2-{1-isopropyl-3-[({4-[(2-methyl-4-quinolinyl)methoxy]phenyl}sulfonyl)methyl]-3-piperidinyl}acetamide;

N-hydroxy-2-{1-isobutyl-3-[({4-[(2-methyl-4-quinolinyl)methoxy]phenyl}sulfonyl)methyl]-3-piperidinyl}acetamide;

N-hydroxy-2-{4-[({4-[(2-methyl-4-quinolinyl)methoxy]phenyl}sulfonyl)methyl]-4-piperidinyl}acetamide;

N-hydroxy-2-{1-methyl-4-[({4-[(2-methyl-4-quinolinyl)methoxy]phenyl}sulfonyl)methyl]-4-piperidinyl}acetamide;

N-hydroxy-2-{2-[({4-[(2-methyl-4-quinolinyl)methoxy]phenyl}sulfonyl)methyl]tetrahydro-2-furanyl}acetamide;

N-hydroxy-2-{1-methyl-3-[({4-[(2-methyl-4-quinolinyl)methoxy]phenyl}sulfonyl)methyl]-2-oxopyrrolidinyl}acetamide;

N-hydroxy-2-{5-[({4-[(2-methyl-4-quinolinyl)methoxy]phenyl}sulfonyl)methyl]-3-(3-pyridinyl)4,5-dihydro-5-isoxazolyl]acetamide;

N-hydroxy-2-{5-[({4-[(2methyl-4-quinolinyl)methoxy]phenyl}sulfonyl)methyl]-3-(4-pyridinyl)-4,5-dihydro-5-isoxazolyl]acetamide and, N-hydroxy-2-{4-[({4-[(2-methyl-4-quinolinyl)methoxy]phenyl}sulfonyl)methyl]tetrahydro-2H-pyran-4-yl}acetamide;

or a pharmaceutically acceptable salt form thereof.

6. A pharmaceutical composition, comprising: a pharmaceutically acceptable carrier and a therapeutically effective amount of a compound according to claim 1 or a pharmaceutically acceptable salt form thereof.

7. A pharmaceutical composition, comprising: a pharmaceutically acceptable carrier and a therapeutically effective amount of a compound according to claim 2 or a pharmaceutically acceptable salt form thereof.

8. A pharmaceutical composition, comprising: a pharmaceutically acceptable carrier and a therapeutically effective amount of a compound according to claim 3 or a pharmaceutically acceptable salt form thereof.

9. A pharmaceutical composition, comprising: a pharmaceutically acceptable carrier and a therapeutically effective amount of a compound according to claim 4 or a pharmaceutically acceptable salt form thereof.

10. A pharmaceutical composition, comprising: a pharmaceutically acceptable carrier and a therapeutically effective amount of a compound according to claim 5 or a pharmaceutically acceptable salt form thereof.

11. A method of treating a disease or condition in a patient, comprising: administering to the mammal in need of such treatment a therapeutically effective amount of a compound of claim 1 or a pharmaceutically acceptable salt form thereof, wherein the disease or condition is selected from cachexia, gingivitis, hemorrhage, multiple sclerosis, neovascular glaucoma, periodontitis, and solid tumor growth and tumor invasion by secondary metastases.

12. A method of treating a disease or condition in a patient, comprising: administering to the mammal in need of such treatment a therapeutically effective amount of a compound of claim 2 or a pharmaceutically acceptable salt form thereof, wherein the disease or condition is selected from cachexia, gingivitis, hemorrhage, multiple sclerosis, neovascular glaucoma, periodontitis, and solid tumor growth and tumor invasion by secondary metastases.

13. A method of treating a disease or condition in a patient, comprising: administering to the mammal in need of such treatment a therapeutically effective amount of a compound of claim 3 or a pharmaceutically acceptable salt form thereof, wherein the disease or condition is selected from cachexia, gingivitis, graft versus host disease, hemorrhage, multiple sclerosis, neovascular glaucoma, periodontitis, and solid tumor growth and tumor invasion by secondary metastases.

14. A method of treating a disease or condition in a patient, comprising: administering to the mammal in need of such treatment a therapeutically effective amount of a compound of claim 4 or a pharmaceutically acceptable salt form thereof, wherein the disease or condition is selected from cachexia, gingivitis, graft versus host disease, hemorrhage, multiple sclerosis, neovascular glaucoma, periodontitis, and solid tumor growth and tumor invasion by secondary metastases.

15. A method of treating a disease or condition in a patient, comprising: administering to the mammal in need of such treatment a therapeutically effective amount of a compound of claim 5 or a pharmaceutically acceptable salt form thereof, wherein the disease or condition is selected from cachexia, gingivitis, graft versus host disease, hemorrhage, multiple sclerosis, neovascular glaucoma, periodontitis, and solid tumor growth and tumor invasion by secondary metastases.

* * * * *